United States Patent
Mikkelsen et al.

(10) Patent No.: US 10,704,080 B2
(45) Date of Patent: Jul. 7, 2020

(54) NUCLEOTIDE SEQUENCE EXCLUSION ENRICHMENT BY DROPLET SORTING (NEEDLS)

(71) Applicant: Samplix ApS, Herlev (DK)

(72) Inventors: Marie Just Mikkelsen, Brønshøj (DK); Thomas Kvist, Roskilde (DK)

(73) Assignee: Samplix ApS, Herlev (DK)

(*) Notice: Subject to any disclaimer, the term of this patent is extended or adjusted under 35 U.S.C. 154(b) by 316 days.

(21) Appl. No.: 15/317,050

(22) PCT Filed: Jun. 11, 2015

(86) PCT No.: PCT/EP2015/063076
§ 371 (c)(1),
(2) Date: Dec. 7, 2016

(87) PCT Pub. No.: WO2015/189336
PCT Pub. Date: Dec. 17, 2015

(65) Prior Publication Data
US 2017/0211127 A1    Jul. 27, 2017

(30) Foreign Application Priority Data
Jun. 11, 2014 (DK) .................... 2014 00307

(51) Int. Cl.
| C12Q 1/68 | (2018.01) |
| C07H 21/00 | (2006.01) |
| C12Q 1/6806 | (2018.01) |
| C12Q 1/6848 | (2018.01) |
| C12Q 1/686 | (2018.01) |

(52) U.S. Cl.
CPC .......... *C12Q 1/6806* (2013.01); *C12Q 1/686* (2013.01); *C12Q 1/6848* (2013.01)

(58) Field of Classification Search
CPC .................. C12Q 1/68; C07H 21/00
See application file for complete search history.

(56) References Cited

U.S. PATENT DOCUMENTS

| 2003/0175701 A1* | 9/2003 | Griffiths ............. C12Q 1/6827 435/6.11 |
| 2007/0077572 A1* | 4/2007 | Tawfik ............... C12N 15/1075 435/6.16 |
| 2008/0014589 A1 | 1/2008 | Link et al. |
| 2010/0069250 A1* | 3/2010 | White, III ............ C12Q 1/6851 506/4 |
| 2011/0071045 A1* | 3/2011 | Patterson ............... G01N 33/53 506/9 |
| 2011/0097763 A1 | 4/2011 | Pollack et al. |
| 2011/0195457 A1 | 8/2011 | Nelson et al. |
| 2011/0217712 A1 | 9/2011 | Hiddessen et al. |
| 2012/0164633 A1 | 6/2012 | Laffler |
| 2013/0165346 A1* | 6/2013 | Wang ..................... G01N 1/28 506/12 |
| 2014/0094373 A1 | 4/2014 | Zimmermann et al. |
| 2017/0121756 A1* | 5/2017 | Abate .................. C12Q 1/686 |
| 2017/0211127 A1* | 7/2017 | Mikkelsen ........... C12Q 1/6806 |

FOREIGN PATENT DOCUMENTS

| EP | 2047910 | 4/2009 |
| EP | 2703497 | 3/2014 |
| WO | WO 2004/083443 | 9/2004 |
| WO | WO 2009140373 | 11/2009 |
| WO | WO 2010018465 | 2/2010 |
| WO | WO 2010/115100 | * 10/2010 |
| WO | WO 2011/100604 | 8/2011 |
| WO | WO 2012/149042 | 11/2012 |
| WO | WO 2013/165748 | 11/2013 |
| WO | WO 2013/181276 | 12/2013 |
| WO | WO 2014/028376 | 2/2014 |

OTHER PUBLICATIONS

Bodin et al., J. of Biomedicine and Biotechnology 3: 248 (Year: 2005).*
Caetano-Anolles, PCR Methods and Applications 3 :85 (Year: 1993).*
Diehl et al., Nature Methods 3(7) : 551 (Year: 2006).*
Fan et al.Analytical Chemistry 79 :7576 (Year: 2007).*
Hosono et al.,Human Mutation 29 (1) :182 (Year: 2008).*
Marcy et al.,. Plos Genetics 3(9) : e155 (Year: 2007).*
Nagesha et al., J. of Virological Methods 60: 147 (Year: 1996).*
Ottesen et al. Science 314 :1464 (Year: 2006).*
Telenius et al., Gene Chromosomes & Cancer 4 :257 (Year: 1992).*
Warren et al., PNAS 103(47) :17807 (Year: 2006).*
Weaver et al., Methods 50 :271 (Year: 2010).*
White III et al., BMC Genomics 10 :116 (Year: 2009).*
Arneson et al., Whole-Genome Amplification by Improved Primer Extension Preamplification PCR (I-PEP-PCR). CSH Protocols 3(1) p. 1-4 (Year: 2008).*
Hedges et al., Comparison of Three Targeted Enrichment Strategies on the SOLiD Sequencing Platform Plos One 6 (4) : e18595. (Year: 2011).*
Mamanova et al., Target-enrichment strategies for nextgeneration sequencing. Nature Methods 7(2) :111 (Year: 2010).*
Markey et al.,High-throughput droplet PCR. Methods 50 :277-281 (Year: 2010).*
Joensson et al., Detection and Analysis of Low-Abundance Cell-Surface Biomarkers Using Enzymatic Amplification in Microfluidic Droplets. Angew. Chem. Int. Ed. 48 : 2518-2521 (Year: 2009).*
Lasken et al., Recent advances in genomic DNA sequencing of microbial species from single cells (Sep. 2014) Nature Reviews| Genetics 15 : 577 (Sep. 2014) (Year: 2014).*
Leung et al., A programmable droplet-based microfluidic device applied to multiparameter analysis of single microbes and microbial communities. PNAS 109(20) : :7665-2670 (Year: 2012).*

(Continued)

Primary Examiner — Ethan C Whisenant
(74) Attorney, Agent, or Firm — Casimir Jones, S.C.; Lisa V. Mueller

(57) ABSTRACT

The present invention pertains to an in vitro method in which a targeted DNA molecule containing a DNA sequence of interest is enriched by a) general amplification of DNA molecules in a multiple of droplets each containing less than 0.5 target DNA molecule on average (404), b) specific detection of the target DNA molecule in each of the droplets (405), and c) physically selecting droplets containing target DNA molecules (406).

15 Claims, 8 Drawing Sheets

Figure 1:
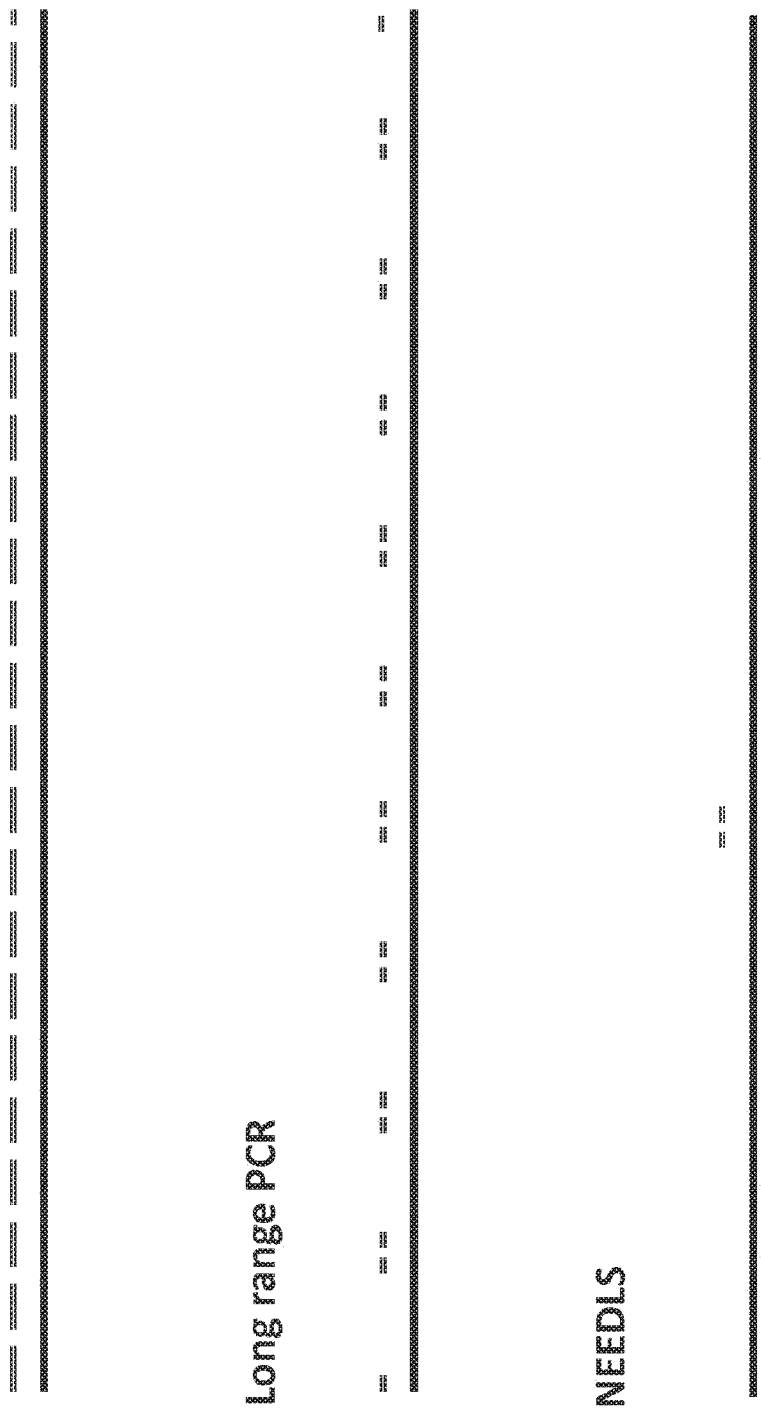

Specification includes a Sequence Listing.

(56) References Cited

OTHER PUBLICATIONS

Mazutis et al., Single-cell analysis and sorting using droplet-based microfluidics. Nature Protocols 8(5) : 870 (Year: 2013).*
Rinke et al., Insights into the phylogeny and coding potential of microbial dark matter. Nature 499 :431 (Year: 2013).*
Ashelford et al., PRIMROSE: a computer program for generating and estimating the phylogenetic range of 16S rRNA oligonucleotide probes and primers in conjunction with the RDP-11 database. Nucleic Acids Res., 2002, 30(15):3481-3489.
Barret et al., "Fluorescence-activated droplet sorting (FADS): efficient microfludic cell sorting based on enzymatic activity,"Lab Chip, 2009. 9(13): p. 1850-8.
Blainey et al., "Digital MDA for enumeration of total nucleaic acid contamination," Nucleic acid research, 2011, vol. 39, No. 4, e 19.
Blainey, "The future is now; Single-cell genomic bacteria and archaea," Fems Microbial Review, 2013, vol. 37, No. 3, pp. 407-427.
Brouzes et al., "Droplet microfluidic technology for single-cell high-throughput screening," Proceedings of the National Academy of Sciences, 2009, 106(34): p. 14185-14200.
Day et al., "Microdroplet Technology: Principles and Emerging Applications in Biology and Chemistry," Integrated analytical systems. ed. R.A. Potyrailo2012.
Garcia-Armisen et al., "Enumeration of viable E. coli in rivers and wastewaters by fluorscent in situ hybridization," J Microbiol. Methods, 2004, 58(2): p. 269-279.
Hatch et al., "1-million droplet array with wide-field flourescence imaging for digital PCR," Lab Chip, 2011, pp. 3838-3845.
Hindson et al., "High-throughput droplet digital PCR system for absolute quantitation of DNA copy number," Anal Chem, 2011, 83(22): p. 8804-8810.
Pan et al., "A procedure for highly specific, sensitive, and unbiased whole-genome amplification," Proceedings of the National Academy of Sciences, 2008, 105( 40): p. 15499-15504.
Prodelalova et al., "Isolation of genomic DNA using magnetic cobalt ferrite and silica particles," Journal of Chromatography A, 2004, 1056(1-2): p. 43-48.
Raghunathan et al., "Genomic DNA amplification from a single bacterium," Applied and Environmental Microbiology, 2005, 71(6): p. 3342-3347.
Rinke et al., "Obtaining genomes from uncultivated environmental microorganisms using FACS-based single-cell genomics," Nat. Protocol. 2014. 9(5): p. 1038-1048.
Sambrook et al., "Molecular Cloning a laboratory manual," 2001, Cold Spring Harbor Laboratory Press.
Sharma et al., "Droplet-based microfluidics," Methods in Molecular Biology, 2013, 949: p. 207-30.
Walter, "Single molecule tools: fluorescence based approaches, part A. Preface," Methods in Enzymology, 2010, 472: p. xxi-xxii.
Yu et al., "Killing two birds with one stone: simultaneous extraction of DNA and RNA from activated sludge biomass," Canadian Journal of Microbiology, 1999, 45(3): p. 269-272.
Zhong et al., "Multiplex digital PCR: breaking the one target per color barrier of quantitative PCR," Lab Chip, 2011, vol. 11, pp. 2167-2174.
Zhu et al., "Single-molecule emuision PCR in microfluidic droplets", Anal Bioanal Chem, 2012, vol. 403, pp. 2127-2143.
Zuker, "Mfold web server for nucleic acid folding and hybridization prediction," Nucleic Acids Res, 2003, 31(13): p. 3406-15.
International Search Report and Written Opinion for Application No. PCT/EP2015/063076 dated Sep. 21, 2015 (9 pages).
Kilstrup et al., "Rapid genome walking: a simplified oligo-cassette mediated polymerase chain reaction using a single genome-specific primer," Nucleic Acids Res, 2000, 28(11 ): p. e55.
Kintses et al., "Microfluidic droplets: new integrated workflows for biological experiments", Curr Opin Chem Bio., 2010, vol. 14, pp. 548-555.
Kvist et al., "Diversity of thermophilc and non-thermophilic crenarchaeota at 80 degrees C," FEMS Microbiol. Lett., 2005, 244(1 ): p. 61-68.
Liu et al., "Comparison of next-generation sequencing systems," J. Biomed Biotechnol, 2012, 2012: p. 251364.
Longo et al., "Use of uracil DNA glycosylase to control carry-over contamination in polymerase chain reactions," Gene, 1990, 93(1): p. 125-8.
Mazutis et al., "Droplet-Based Microfluidic Systems for High-Throughput Single DNA Molecule Isothermal Amplification and Analysis," Analytical Chemistry, 2009, vol. 81, No. 12, pp. 4813-4821.

* cited by examiner

SEQUENCE LISTING

```
<160> NUMBER OF SEQ ID NOS: 14

<210> SEQ ID NO 1
<211> LENGTH: 25
<212> TYPE: DNA
<213> ORGANISM: Unknown
<220> FEATURE:
<223> OTHER INFORMATION: Description of Unknown: Bacterium sequence
<220> FEATURE:
<221> NAME/KEY: primer_bind
<222> LOCATION: (1)..(25)
<223> OTHER INFORMATION: Lip-Fw primer for a bacterial lipase gene

<400> SEQUENCE: 1
ctgaatgggg gaataatgac aagcc                                           25

<210> SEQ ID NO 2
<211> LENGTH: 26
<212> TYPE: DNA
<213> ORGANISM: Unknown
<220> FEATURE:
<223> OTHER INFORMATION: Description of Unknown: Bacterium sequence
<220> FEATURE:
<221> NAME/KEY: primer_bind
<222> LOCATION: (1)..(26)
<223> OTHER INFORMATION: Lip-Re primer for a bacterial lipase gene

<400> SEQUENCE: 2
ctatactctt cttttaattc ctcagc                                          26

<210> SEQ ID NO 3
<211> LENGTH: 20
<212> TYPE: DNA
<213> ORGANISM: Staphylococcus sp.
<220> FEATURE:
<221> NAME/KEY: primer_bind
<222> LOCATION: (1)..(20)
<223> OTHER INFORMATION: Staph-Fw primer for 16S rDNA in Staphylococcus
      sp

<400> SEQUENCE: 3
agactgggat aacttcggga                                                 20
```

<210> SEQ ID NO 4
<211> LENGTH: 23
<212> TYPE: DNA
<213> ORGANISM: Staphylococcus sp.
<220> FEATURE:
<221> NAME/KEY: primer_bind
<222> LOCATION: (1)..(23)
<223> OTHER INFORMATION: Staph-Re primer for 16S rDNA in Staphyloccus sp

<400> SEQUENCE: 4
cgtctttcac ttttgaacca tgc                                            23

<210> SEQ ID NO 5
<211> LENGTH: 21
<212> TYPE: DNA
<213> ORGANISM: Thermoanaerobacter italicus
<220> FEATURE:
<221> NAME/KEY: primer_bind
<222> LOCATION: (1)..(21)
<223> OTHER INFORMATION: GAP-Fw-1 primer for genome of
      Thermoanaerobacter italicus

<400> SEQUENCE: 5
gaagggtgac aggattgata c                                              21

<210> SEQ ID NO 6
<211> LENGTH: 22
<212> TYPE: DNA
<213> ORGANISM: Thermoanaerobacter italicus
<220> FEATURE:
<221> NAME/KEY: primer_bind
<222> LOCATION: (1)..(22)
<223> OTHER INFORMATION: GAP-Re-1 primer for Thermoanaerobacter italicus
      genome

<400> SEQUENCE: 6
cggatttcct cctttctatt cc                                             22

<210> SEQ ID NO 7
<211> LENGTH: 24
<212> TYPE: DNA
<213> ORGANISM: Thermoanaerobacter italicus
<220> FEATURE:
<221> NAME/KEY: primer_bind
<222> LOCATION: (1)..(24)
<223> OTHER INFORMATION: GAP-Fw-2 primer for Thermoanaerobacter italicus
      genome

<400> SEQUENCE: 7
gccttgcaaa ttctacattg acag                                           24

<210> SEQ ID NO 8
<211> LENGTH: 25
<212> TYPE: DNA
<213> ORGANISM: Thermoanaerobacter italicus
<220> FEATURE:
<221> NAME/KEY: primer_bind
<222> LOCATION: (1)..(25)
<223> OTHER INFORMATION: GAP-Re-2 primer for Thermoanaerobacter italicus
      genome

<400> SEQUENCE: 8
ccaagaaaat catgggagat agttc                                          25

<210> SEQ ID NO 9
<211> LENGTH: 5201
<212> TYPE: DNA
<213> ORGANISM: Thermoanaerobacter italicus
<220> FEATURE:
<221> NAME/KEY: gene
<222> LOCATION: (1)..(5201)
<223> OTHER INFORMATION: Sequence in Thermoanaerobacter italicus genome

<400> SEQUENCE: 9

| | | | | | |
|---|---|---|---|---|---|
| ttgaaaatta | ctctactatc | tttaatgatt | tttattatga | ttttggagg | aattacttcg | 60 |
| gcatacgctt | acgacaaaat | ccacgttgtt | tcaaaaggtg | agtcgctata | tttaatagct | 120 |
| aaatggtatg | gaagtgatgt | aaatagccta | aagaggtaa | atggaaaatg | gagtgatttg | 180 |
| atatatcccg | gtgaaaaatt | agttgtgcca | gtaaacgtaa | acactgctta | ttacaattat | 240 |
| cttgctgata | gatatttaat | tgcaaaaatg | atttatgctg | aagctcgagg | agaaagcttg | 300 |
| gaaggccaag | tagctgtagg | tgcggtaatt | ttgaatagag | taaaaagtaa | tattttccca | 360 |
| gatactgtag | caggagttat | atatcagtca | gatgcttttg | agtctataac | aaatggcgag | 420 |
| tttttcaatc | acgagcctga | ccttacagct | tttaaagcgg | cagatttagc | tttagctgga | 480 |
| tgggacccaa | cgggtggagc | actatacttt | ttcaatccgg | ctacttcaac | ttcttggtgg | 540 |
| atatggacaa | ggacagttac | taatgtcata | gggaaccact | ggtttgcaat | atagaaaggc | 600 |
| gtcctgcctt | tctatattgc | atgtatttta | cattataaaa | ttttactttt | gtaaaagaat | 660 |
| aagaatagca | ctaaaaatag | gagctgatca | tatggtatat | attttgtag | gaggaagttc | 720 |
| ggaaaaaagt | ttgcttataa | gattttttatc | ctactgtgta | aattctaaag | aaacagtaat | 780 |
| aggacagtta | aaaaattata | atgagagagc | agatattttg | attatttctg | atattttaaa | 840 |
| cgaggaagat | tttaacaagt | taaaaaatta | tatttatagc | tttccaagca | gtattataat | 900 |
| aacaaatgga | gatgatgagc | tatcaaataa | actctttgca | aaaggaataa | attctaccct | 960 |
| tataacatgc | ggtttgaatc | caaaatcttc | cattactgct | tcttcaatat | cctatgaaga | 1020 |
| agagggctat | gaatttaatt | attgcgtaca | aagggctttt | tttaatttaa | agggtaaatt | 1080 |
| aatagaacca | ttggaaatac | ctgttgaaat | aaaagtttct | gaacagtata | atatatgta | 1140 |
| ctcattgttt | gtaataactg | tattattgat | tttaggaaat | gaaataaaag | atatacaaaa | 1200 |
| tgtagttaaa | acctttaaag | atagtggata | gtggcaattt | tttaaaaatt | aattttagaa | 1260 |
| attacctttt | actatctgtc | ataaatgctt | tctaattta | atatatattt | ttagaagata | 1320 |
| cataagggga | aggggagagt | gaacacatgg | caggcaactt | tttggagaac | aacgtagttg | 1380 |
| tagtggtggg | gagaattttt | actgatttag | agtatagcca | tcaactatat | ggggaaaaat | 1440 |
| tttttaattt | tattttggaa | gttccaagat | tgagtgagac | gaaagattat | cttcctgtca | 1500 |
| ctatttctaa | ccgtttattt | gaaggcatga | atttagaggt | tggtacaagg | ataaagattg | 1560 |
| aagggcaatt | aaggtcttac | aataggaaat | caccagaaga | ggggaaaaat | aagttgatat | 1620 |
| taaccatatt | tgctcgagat | ataatggcat | tgtcagaaga | ggaaatagta | aaaaatccga | 1680 |
| atgaaatttt | tttggatggc | tttatttgta | aaaaacctgt | ttatagaact | actccttag | 1740 |
| gaagagaaat | aaccgattta | ttaattgctg | taaataggcc | ttataacaaa | tctgattaca | 1800 |
| tacctgttat | agcgtggggg | agaaatgcga | ggttttctga | aagttggaa | ataggagatc | 1860 |
| gtatacgctt | gtggggaaga | gtacagagta | gggaatatca | gaaaaactg | ggcgatgaag | 1920 |
| tggctacaaa | ggtagcttat | gaggtttcta | ttacaagaat | ggaagtggtt | gaaaagaat | 1980 |
| tgcaaaagag | ttagaatgga | agtaacggag | gacaaaagga | ggaataaatt | ttggaaagag | 2040 |
| gacttataca | agtttatact | ggagacggca | agggaagac | taccgcttct | attggtcttg | 2100 |
| gcataagggc | agtgggaaga | ggatttaaag | tatatatggt | acaattttta | aaaggagcag | 2160 |

```
atacaggaga acttcataca cttaagaata ttgaaaattt taaagttttt aggtttcagt    2220
ccacaaataa atttttttgg acattgacgg aagaagagaa aaaaatcctc gcggaagaca    2280
tgaaaaaagc ctatgatttt gtagtagagg tgcttaaaaa caaaaaatgt gatgtcctta    2340
ttttagatga gataatggcg gcaatatata gcaagatgta cactgtagag gatgtgttaa    2400
aattaataga tatgaaacct aaagagatgg aacttgtttt gacaggtaga agtgctcctc    2460
aagaaattat tgaaagggcg gatttggtta cagaaatgaa agcaattaaa catccatttg    2520
aaaagggaat accagcaaga tacggtatag aatactaaaa cacccgaaaa atcgggtgtt    2580
ttaattaacc tcttaagtct tccatgagtt ttgttttttc acgagttttg tcatctacta    2640
cttttacaat tttagctgga actcctgcga ctactgtgtt aggtggtaca tcttctgtca    2700
ccactgaacc tgctgctaca acagcgccat ggcctactct tactccttct aatatgactg    2760
catttgctcc gacaagtacg ttatcttcaa gcacaaccgg cacgctgcta ggaggttcca    2820
atacacctgc tattacagct ccagctccta catggacgtt tttgcctata attcctctag    2880
cgcctattac tgcgttcatg tctatcatag aattttcacc aatttctgca cctatatttta   2940
tcactgctcc catcataatc acagcgtttt tgcctatttt gactttatct ctaattattg    3000
cccctggttc tattctcgcg tcaagatgct taatatccag taaaggaatt gcagagtttc    3060
tgcgatcata ctctagatga taatgtttta ttttatcttt gtttgcttca atcaattttt    3120
ccacgacatc tagttctcca aaaataactt taaagttatc acagccatat acttctaatt    3180
cttcggtttc tttaatttct atattcccctt gtatgtaagc tctaacgggc gttgactttt    3240
ttgcctcttt aatgtatctt gcaatttcat aaggatttgt taaattatca tttgtactca    3300
aatactatca tccttttcttt acaaggtctt ccatgctgta taacccaggt ttttgaccta    3360
ttatgaattt tgcagcatgt agggcaccat agccaaaaat ttcgcgggat tgggcagagt    3420
gacttatggt gattacttca tcgtgaccag caaaaattac ttggtgctca cccacaattg    3480
tgcctcccct tactgcatgt atccctaatt cattcgtttt tctctgttca gttttagtat    3540
ggcgtccata cacgtattct ttttttgtcat ttagtacttg gtttatgcta tctgcaatca    3600
ttaacgcagt gccacttgga gcatcttttt tcatattgtg atgtttctct attatttcta    3660
tgtcaaaatc ttgctgcaat attttttgcag cttctttttac aaggtttata agaatattca    3720
ctccaaggga catatttgca gatttgaaaa ttggtatttc ttttgatgca tgttttatga    3780
catttaattc ttcttcactg agtcctgttg tggcaatgac tacaggaagt ttcttttgta    3840
gagcggcttt tactaaatta ggtacagctt catggtatga aaagtcaatt actacatccg    3900
cttcttcttt tacatctttt aaatcgctgt aaacaggaaa gtcaagagga gagatgtttt    3960
tatctactcc tgctactatt ttaaaatcgg gactttctgc tgctaacttt gctacgactt    4020
ttcccatttt tccgttacag ccgtgaatta ttattctaat cattaatttg cctccttcaa    4080
taaaccgtat tttgaaagaa cagatttcag atattctaag tttttatcgc tcatttcaac    4140
aagtgggagg cgcaaaggtc ctacgttgaa tcccattaag ttcatagcag ttttttacagg    4200
aatagggttt gtttctacga aaagtgcttt attcagaggg ttaagttcta attgcatgtt    4260
tcttgccttt tcaatgtccc catttaaata agcggttgtc atctcatgta ttttttgccgg    4320
gattatattt gccgtgacag atattacgcc taagccccct aaagacatta ttggtattac    4380
ttggtcgtca tttcctgagt atatttcgaa agatttaccc ataatacggg caatttcagc    4440
tacttgtaca atgtcaccac tggcttcttt taccccaact acgttgtcta catgtttact    4500
taattcaaga taagtttctg gcaacatatt aagagatgtc ctgcttggga cattatagat    4560
```

```
aataataggt atatctacgt gtcttgctat ttcagtaaaa tgagccacta atccctttg    4620 tgttgttttg ttgtaatatg gtgttataac taaaagagca tcagcacctg cagattgagc    4680
atattcactc atttcaacgg catgggctgt attgttagaa ccggtccctg caattattgg    4740
tattcttccg gcaacttttt caacggtaaa tttgattgcc gcttgttgct cttcttgtgt    4800
cattgtagag gcttcaccag tggtaccaca tatgatgatt gcatcagttc cttctttgat    4860
atgccattca ataagctcgc caagttttc aaaatttacg ccctcttcat taaatggagt    4920
aacaatagcg acacctgacc ctttaaaaac aggcataatt attctccttt cacatatttt    4980
taattaaaag ttctgctatt tgaacggcgt ttgtagctgc cccttttctt atgttgtcag    5040
ctacaatcca catattaaga ccgctgtaaa ctgtctcatc tcgtcttatt ctacctacaa    5100
aaacttcatc ttttcctgtg gcataagttg caagaggata aatattattt tgaggatcgt    5160
cttgtacaac aactcctgga gcatgtttta agacctctat t                        5201

<210> SEQ ID NO 10
<211> LENGTH: 4816
<212> TYPE: DNA
<213> ORGANISM: Staphyloccccus sp.
<220> FEATURE:
<221> NAME/KEY: gene
<222> LOCATION: (1)..(4816)
<223> OTHER INFORMATION: Staph 16S+ITS+23S gene encoding rRNA

<400> SEQUENCE: 10
ttttatggag agtttgatcc tggctcagga tgaacgctgg cggcgtgcct aatacatgca      60
agtcgagcga acggacgaga agcttgcttc tctgatgtta gcggcggacg ggtgagtaac     120
acgtggataa cctacctata agactgggat aacttcggga aaccggagct aataccggat     180
aatattttga accgcatggt tcaaaagtga agacggtct tgctgtcact tatagatgga     240
tccgcgctgc attagctagt tggtaaggta acggcttacc aaggcaacga tgcatagccg     300
acctgagagg gtgatcggcc acactggaac tgagacacgg tccagactcc tacgggaggc     360
agcagtaggg aatcttccgc aatgggcgaa agcctgacgg agcaacgccg cgtgagtgat     420
gaaggtcttc ggatcgtaaa actctgttat tagggaagaa catatgtgta agtaactgtg     480
cacatcttga cggtacctaa tcagaaagcc acggctaact acgtgccagc agccgcggta     540
atacgtaggt ggcaagcgtt atccggaatt attgggcgta aagcgcgcgt aggcggtttt     600
ttaagtctga tgtgaaagcc cacggctcaa ccgtggaggg tcattggaaa ctggaaaact     660
tgagtgcaga agaggaaagt ggaattccat gtgtagcggt gaaatgcgca gagatatgga     720
ggaacaccag tggcgaaggc gactttctgg tctgtaactg acgctgatgt gcgaaagcgt     780
ggggatcaaa caggattaga taccctggta gtccacgccg taaacgatga gtgctaagtg     840
ttagggggtt tccgccccct tagtgctgca gctaacgcatt aagcactccg cctggggagt     900
acgaccgcaa ggttgaaact caaaggaatt gacgggacc cgcacaagcg gtggagcatg     960
tggtttaatt cgaagcaacg cgaagaacct taccaaatct tgacatcctt tgacaactct    1020
agagatagag ccttcccctt cggggggacaa agtgacaggt ggtgcatggt tgtcgtcagc    1080
tcgtgtcgtg agatgttggg ttaagtcccg caacgagcgc aacccttaag cttagttgcc    1140
atcattaagt tgggcactct aagttgactg ccggtgacaa accggaggaa ggtggggatg    1200
acgtcaaatc atcatgcccc ttatgatttg ggctacacac gtgctacaat ggacaataca    1260
aagggcagcg aaaccgcgag gtcaagcaaa tcccataaag ttgttctcag ttcggattgt    1320
```

```
agtctgcaac tcgactacat gaagctggaa tcgctagtaa tcgtagatca gcatgctacg   1380
gtgaatacgt tcccgggtct tgtacacacc gcccgtcaca ccacgagagt ttgtaacacc   1440
cgaagccggt ggagtaacct tttaggagct agccgtcgaa ggtgggacaa atgattgggg   1500
tgaagtcgta acaaggtagc cgtatcggaa ggtgcggctg gatcacctcc tttctaagga   1560
tatattcgga acatcttctt cagaagatgc ggaataacgt gacatattgt attcagtttt   1620
gaatgtttat ttaacattca aaaaatggg cctatagctc agctggttag agcgcacgcc   1680
tgataagcgt gaggtcggtg gttcgagtcc acttaggccc accattattt gtacattgaa   1740
aactagataa gtaagtaaaa tatagatttt accaagcaaa accgagtgaa taaagagttt   1800
taaataagct tgaattcata agaaataatc gctagtgttc gaaagaacac tcacaagatt   1860
aataacgcgt ttcctgtagg atggaaacat agattaagtt attaagggcg cacggtggat   1920
gccttggcac tagaagccga tgaaggacgt tactaacgac gatatgcttt ggggagctgt   1980
aagtaagctt tgatccagag atttccgaat ggggaaaccc agcatgagtt atgtcatgtt   2040
atcgatatgt gaatacatag catatcagaa ggcacacccg gagaactgaa acatcttagt   2100
acccggagga agagaaagaa aattcgattc ccttagtagc ggcgagcgaa acgggaagag   2160
cccaaaccaa caagcttgct tgttgggggtt gtaggacact ctatacgag ttacaaagga   2220 cgacattaga cgaatcatct ggaaagatga atcaaagaag gtaataatcc tgtagtcgaa   2280
aatgttgtct ctcttgagtg gatcctgagt acgacggagc acgtgaaatt ccgtcggaat   2340
ctgggaggac catctcctaa ggctaaatac tctctagtga ccgatagtga accagtaccg   2400
tgagggaaag gtgaaaagca ccccggaagg ggagtgaaat agaacctgaa accgtgtgct   2460
tacaagtagt cagagcccgt taatgggtga tggcgtgcct tttgtagaat gaaccggcga   2520
gttacgattt gatgcaaggt taagcagtaa atgtggagcc gtagcgaaag cgagtctgaa   2580
tagggcgttt agtatttggt cgtagacccg aaaccaggtg atctacccctt ggtcaggttg   2640 aagttcaggt aacactgaat ggaggaccga accgacttac gttgaaaagt gagcggatga   2700
actgagggta gcggagaaat tccaatcgaa cctggagata gctggttctc tccgaaatag   2760
ctttagggct agcctcaagt gatgattatt ggaggtagag cactgttttgg acgaggggcc   2820 cctctcgggt taccgaattc agacaaactc cgaatgccaa ttaatttaac ttgggagtca   2880
gaacatgggt gataaggtcc gtgttcgaaa gggaaacagc ccagaccacc agctaaggtc   2940
ccaaaatata tgttaagtgg aaaaggatgt ggcgttgccc agacaactag gatgttggct   3000
tagaagcagc catcatttaa agagtgcgta atagctcact agtcgagtga cactgcgccg   3060
aaaatgtacc ggggctaaac atattaccga agctgtggat tgtcctttgg acaatggtag   3120
gagagcgttc taagggcgtt gaagcatgat cgtaaggaca tgtggagcgc ttagaagtga   3180
gaatgccggt gtgagtagcg aaagacgggt gagaatcccg tccaccgatt gactaaggtt   3240
tccagaggaa ggctcgtccg ctctgggtta gtcgggtcct aagctgaggc cgacaggcgt   3300
aggcgatgga taacaggttg atattcctgt accacctata atcgttttaa tcgatggggg   3360
gacgcagtag gataggcgaa gcgtgcgatt ggattgcacg tctaagcagt aaggctgagt   3420
attaggcaaa tccggtactc gttaaggctg agctgtgatg gggagaagac attgtgtctt   3480
cgagtcgttg atttcacact gccgagaaaa gcctctagat agaaaatagg tgcccgtacc   3540
gcaaaccgac acaggtagtc aagatgagaa ttctaaggtg agcgagcgaa ctctcgttaa   3600
ggaactcggc aaaatgaccc cgtaacttcg ggagaagggg tgctctttag ggttaacgcc   3660
cagaagagcc gcagtgaata ggcccaagcg actgtttatc aaaaacacag gtctctgcta   3720
```

```
aaccgtaagg tgatgtatag gggctgacgc ctgcccggtg ctggaaggtt aagaggagtg    3780
gttagcttct gcgaagctac gaatcgaagc cccagtaaac ggcggccgta actataacgg    3840
tcctaaggta gcgaaattcc ttgtcgggta agttccgacc cgcacgaaag gcgtaacgat    3900
ttgggcactg tctcaacgag agactcggtg aaatcatagt acctgtgaag atgcaggtta    3960
cccgcgacag gacggaaaga ccccgtggag ctttactgta gcctgatatt gaaattcggc    4020
acagcttgta caggataggt aggagccttt gaaacgtgag cgctagctta cgtgpaggcg    4080 ctggtgggat actaccctag ctgtgttggc tttctaaccc gcaccactta tcgtggtggg    4140
agacagtgtc aggcgggcag tttgactggg gcggtcgcct cctaaaaggt aacgaggcg     4200 ctcaaaggtt ccctcagaat ggttggaaat cattcataga gtgtaaaggc ataagggagc    4260
ttgactgcga gacctacaag tcgagcaggg tcgaaagacg gacttagtga tccggtggtt    4320
ccgcatggaa gggccatcgc tcaacggata aaagctaccc cggggataac aggcttatct    4380
cccccaagag ttcacatcga cggggaggtt tggcacctcg atgtcggctc atcgcatcct    4440
ggggctgtag tcggtcccaa gggttgggct gttcgcccat taaagcggta cgcgagctgg    4500
gttcagaacg tcgtgagaca gttcggtccc tatccgtcgt gggcgtagga aatttgagag    4560
gagctgtcct tagtacgaga ggaccgggat ggacatacct ctggtgtacc agttgtcgtg    4620
ccaacggcat agctgggtag ctatgtgtgg acgggataag tgctgaaagc atctaagcat    4680
gaagcccccc tcaagatgag atttcccaac ttcggttata agatccctca agatgatga    4740 ggttaatagg ttcgaggtgg aagcatggtg acatgtggag ctgacgaata ctaatcgatc    4800
gaagacttaa tcaaaa                                                    4816

<210> SEQ ID NO 11
<211> LENGTH: 22
<212> TYPE: DNA
<213> ORGANISM: Escherichia coli
<220> FEATURE:
<221> NAME/KEY: primer_bind
<222> LOCATION: (1)..(22)
<223> OTHER INFORMATION: MB8 fw1 primer for thrA gene

<400> SEQUENCE: 11
gacggtagat tcgaggtaat gc                                               22

<210> SEQ ID NO 12
<211> LENGTH: 20
<212> TYPE: DNA
<213> ORGANISM: Escherichia coli
<220> FEATURE:
<221> NAME/KEY: primer_bind
<222> LOCATION: (1)..(20)
<223> OTHER INFORMATION: MB8 Re1 primer for thrA gene

<400> SEQUENCE: 12
tatggccggc gtattagaag                                                  20

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: stem_loop
<222> LOCATION: (1)..(35)
<223> OTHER INFORMATION: molecular beacon for ThrA primers
```

```
<400> SEQUENCE: 13
cgtttgtgtt ttcgaccgga tcgataacag taacg                              35

<210> SEQ ID NO 14
<211> LENGTH: 97
<212> TYPE: DNA
<213> ORGANISM: Escherichia coli
<220> FEATURE:
<221> NAME/KEY: gene
<222> LOCATION: (1)..(97)
<223> OTHER INFORMATION: Sequence in ThrA gene

<400> SEQUENCE: 14
gacggtagat tcgaggtaat gccccactgc cagcagtttt tcgaccggat cgataacagt   60
aacgttgtga ccgcgcgctt ctaatacgcc ggccata                            97
```

NUCLEOTIDE SEQUENCE EXCLUSION ENRICHMENT BY DROPLET SORTING (NEEDLS)

SEQUENCE LISTING

The instant application contains a Sequence Listing which has been submitted electronically in ASCII format and is hereby incorporated by reference in its entirety. Said ASCII copy, created on Mar. 22, 2017, is named 030547-9055-US01_SL.txt and is 17,021 bytes in size.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 16,844 Byte ASCII (Text) file named "030547-9055-US00_Seq_Listing" created on Dec. 7, 2016.

CROSS-REFERENCE TO RELATED APPLICATIONS

This is a U.S. national stage entry of International Patent Application No. PCT/EP2015/063076, filed on Jun. 11, 2015, which claims priority to Danish Patent Application No. PA201400307, filed on Jun. 11, 2014, the entire contents of all of which are fully incorporated herein by reference.

TECHNICAL FIELD

The invention relates to a method for enrichment or isolation of a complex nucleotide fragment comprising a known nucleotide sequence element, i.e. a sequence encoding a conserved active site or domain, the method being applicable i.a. to high throughput screening for DNA fragments containing a known sequence element.

BACKGROUND OF THE INVENTION

Sequencing of DNA is a major driver in genetics research. The 'next generation sequencing' technological revolution is gathering momentum as new robust high-throughput sequencing instruments are becoming available. New and improved methods and protocols have been developed to support a diverse range of applications, including analysis of genetic variation. As part of this, methods have been developed that aim to achieve targeted enrichment of genome sub-regions such as targeted cancer panels or complete human exomes. By selective recovery of genomic loci of interest, costs and effort can be reduced significantly compared with whole-genome sequencing.

Current techniques for targeted enrichment fall into three categories; Hybrid capture, selective circularization, and PCR amplification. In hybrid capture techniques, short fragment libraries (typically 100-250 base pairs) are hybridized specifically to complementary DNA fragments so that one can physically capture and isolate the sequences of interest. Selective circularization describes methods wherein single-stranded DNA circles including target sequences are formed, creating structures with common DNA elements that are then used for selective amplification of the target sequence. Finally, PCR amplification based enrichment is directed toward the target region by conducting multiple long range PCR reactions in parallel.

Common for the current enrichment methods is that they require a significant knowledge of the target sequence, a relatively pure sample and a significant amount of target sequence.

SUMMARY OF THE INVENTION

The present invention provides an in vitro method for enriching one of more target DNA molecule from a sample of mixed DNA molecules comprising the steps of:
  a) providing a liquid sample of mixed DNA molecules comprising one or more target DNA molecule and reagents for general amplification of DNA (401),
  b) formation of a multiple of liquid droplets each comprising mixed DNA molecules from said liquid sample (403),
  c) general amplification of the mixed DNA molecules in the multiple of droplets, wherein each droplet contains less than 0.5, preferably less than 0.25 or even more preferably less than 0.1 of said one or more target DNA molecule on average (404),
  d) specific detection of droplets containing at least one of said target DNA molecule (405), and
  e) selecting droplets containing at least one of said target DNA molecule (406); wherein the frequency of the target DNA molecule compared to its frequency in the sample of mixed DNA molecules in step (a) is increased between $0.1 \times$(number of droplets without target DNA)$\times$(number of droplets with target DNA)$^{-1}$ and $10 \times$(number of droplets without target DNA)$\times$(number of droplets with target DNA)$^{-1}$.

In a further embodiment the invention provides an apparatus for enriching one or more target DNA molecule from a sample of mixed DNA molecules, the apparatus comprising components for:
  a) generation of droplets containing the sample of mixed DNA molecules,
  b) isothermal incubation,
  c) merging the droplets with reagents for detection of the one or more target DNA molecule, and
  d) specific detection and physical selection of droplets comprising at least one of the target DNA molecule.

LEGENDS TO THE FIGURES

FIG. 1: Comparison of Droplet Exclusion Enrichment to current methods of specific DNA enrichment. The filled black lines represent a DNA target of approximately 10 kb. The dotted lines represent the nucleotide sequence information in respect of the target sequence that is needed in advance in order to perform the enrichment. The nucleotide sequence information required for NEEDLS can be located at any position on the DNA target sequence.

Figure 2:
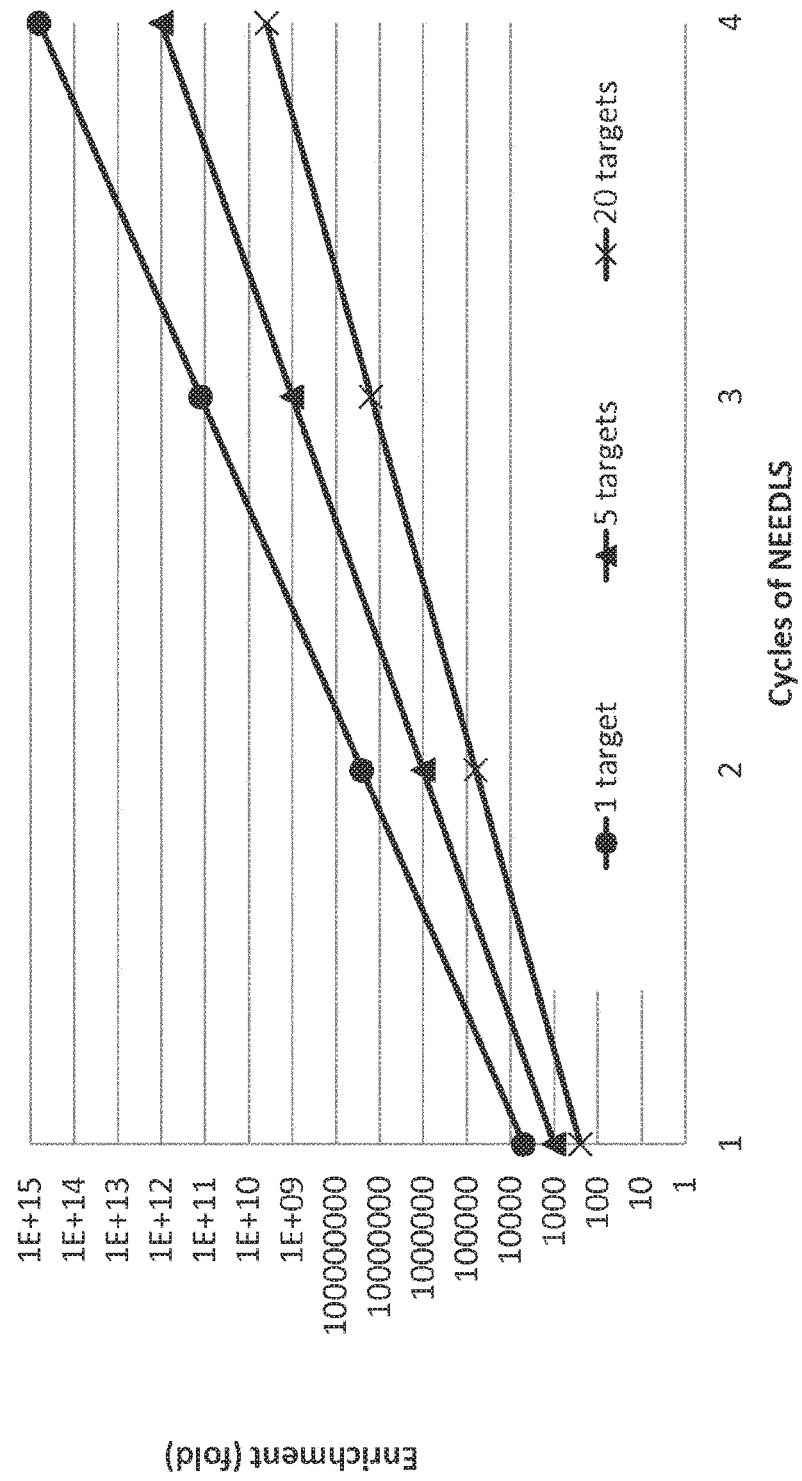

FIG. 2: Enrichment of target DNA (fold) after 1, 2, 3, and 4 rounds of NEEDLS shown for 1, 5 and 20 targets multiplexed in one reaction assuming four positive droplets per target sequence and a total of 20,000 droplets.

Figure 3:
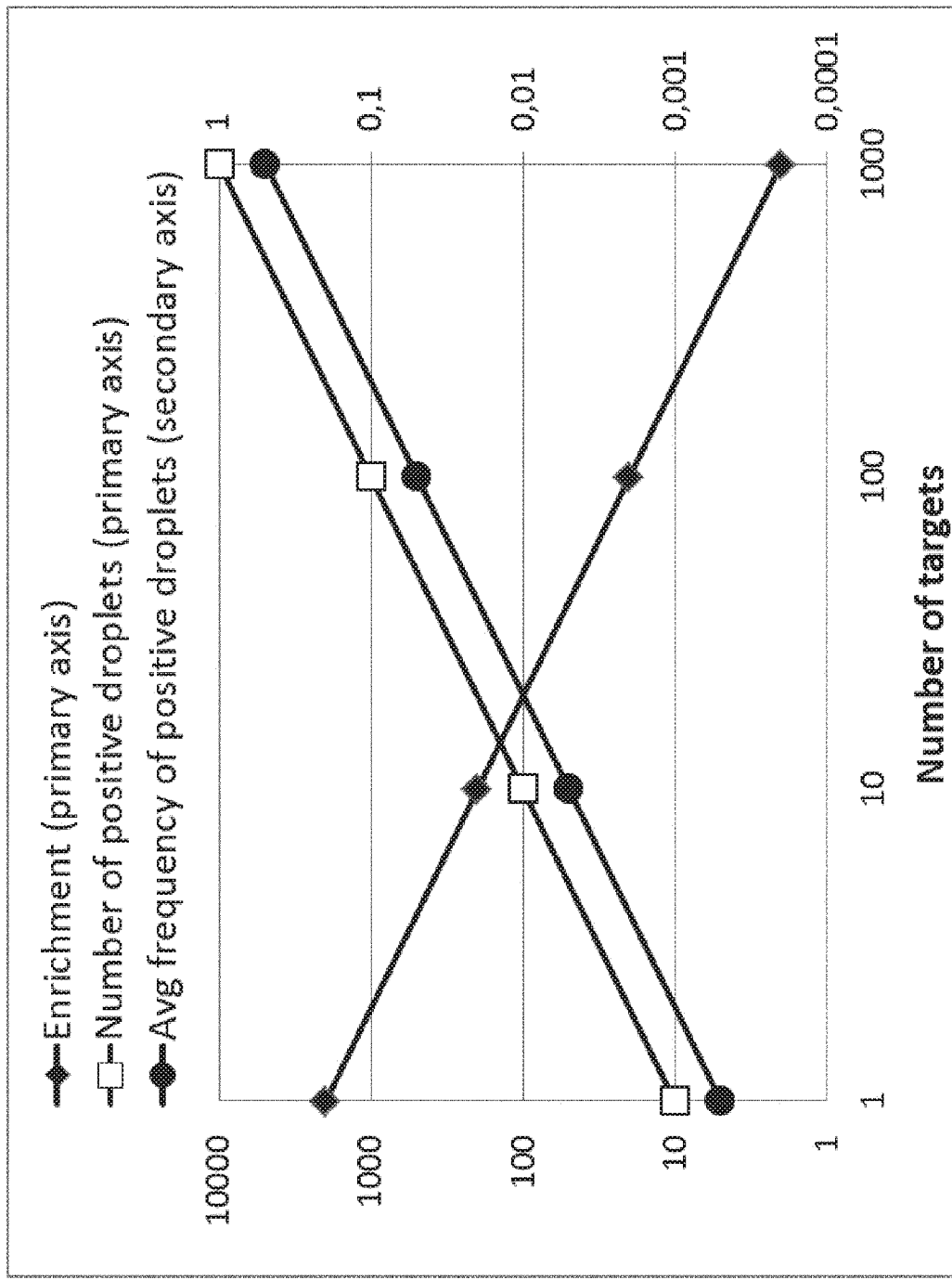

FIG. 3: Correlation between number of targets, the average number of positive droplets and the resulting target enrichment. Here exemplified using one round of NEEDLS, 20,000 droplets and 10 positive droplets per target.

Figure 4:
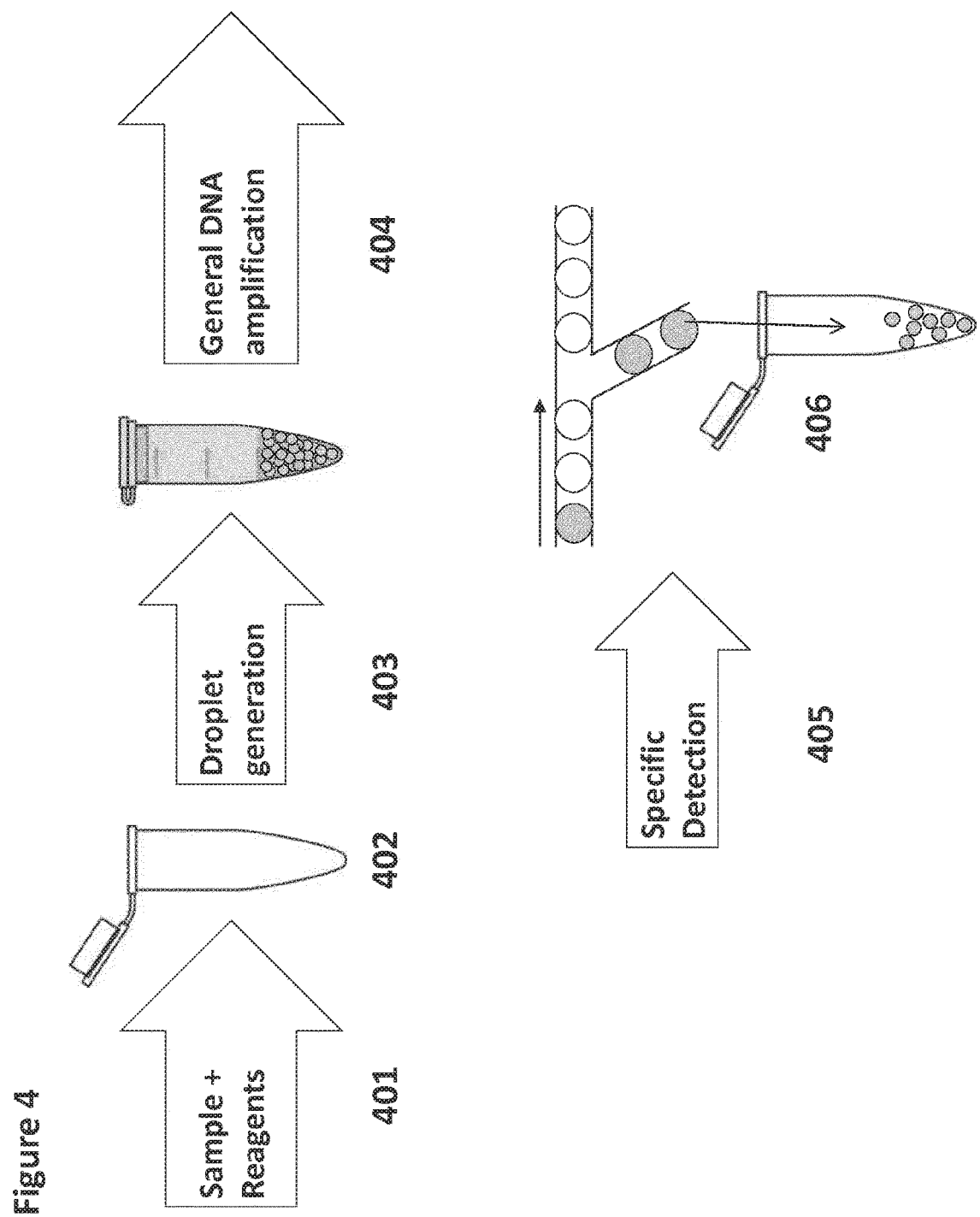

FIG. 4: Outline of a scheme for performing NEEDLS
  401: DNA sample containing one or more DNA target and reagents for general amplification are mixed.
  402: Components required for droplet generation are added to the mixture.

403: Droplets containing the DNA and reagents are generated.
404: General DNA amplification is carried out on all droplets.
405: Specific amplification to detect the one or more target DNA is performed on DNA amplified on each droplet.
406: Droplets, where a specific amplification is detected are isolated using an apparatus for physical selection of droplets.

Figure 5:
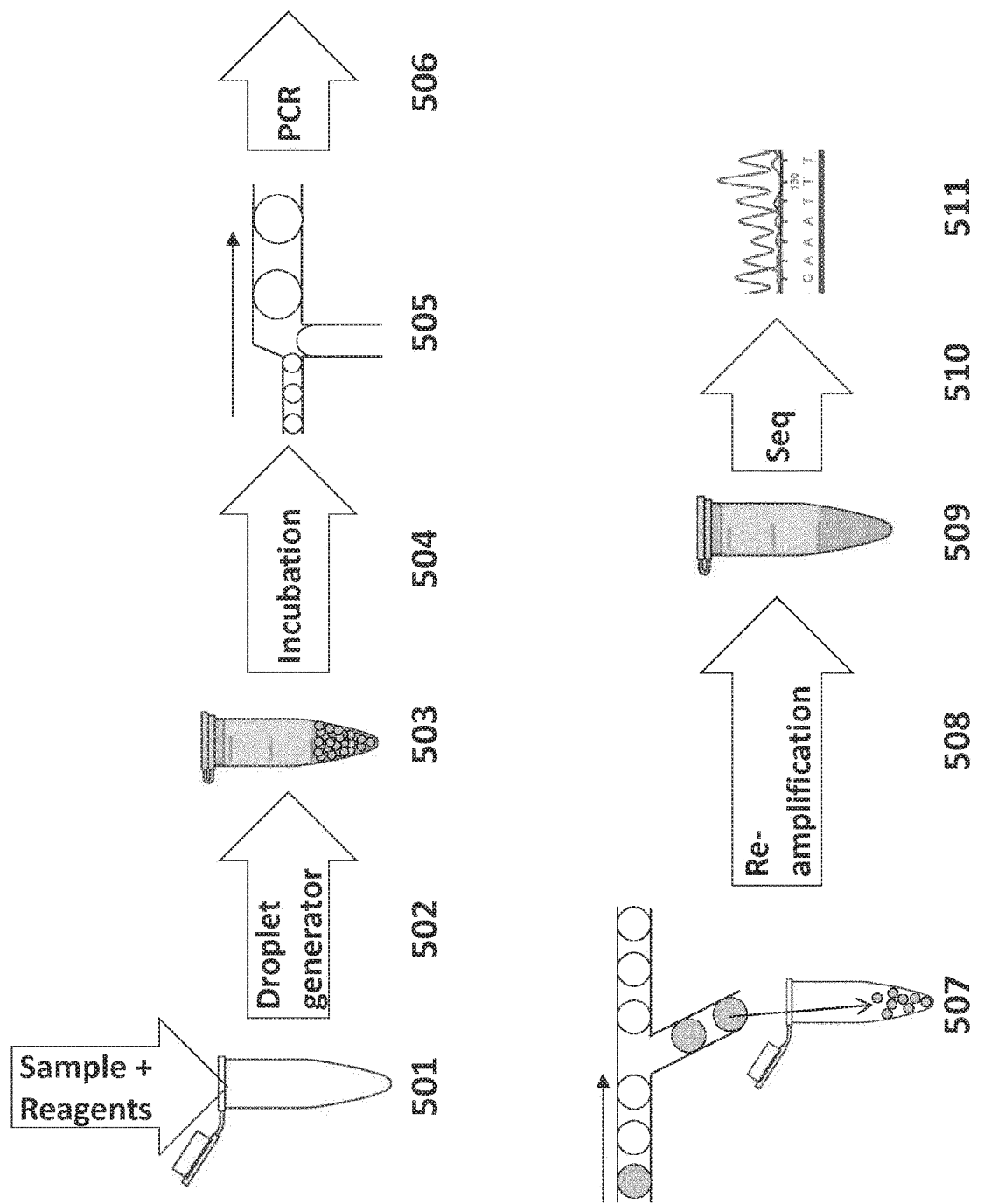

FIG. 5: Outline of a scheme for performing NEEDLS as described in Example 1.
501: Mixing of template DNA, reagents for general DNA amplification and a component required for droplet generation.
502: All material from (501) is converted into droplets of approx. 1 nL each.
503: All droplets are collected in one tube.
504: The droplets are incubated under conditions suitable for general DNA amplification.
505: Droplets are aligned and individually merged with a surplus of liquid comprising a complete dUTP-PCR mixture for selective target DNA amplification and all droplets are collected in a PCR-tube.
506: The PCR tube is incubated under PCR reaction conditions.
507: The droplets in which a specific amplification has taken place are collected and the droplet generating component (e.g. oil) is removed. Uracil-DNA Glycosylase (UDG) treatment can be used to inactivate all PCR generated DNA into which uracil is incorporated. The DNA content is purified by ethanol precipitation.
508: The precipitated DNA (507) is re-amplified.
509: The re-amplified DNA (508) is used as template for a final analysis.
510: DNA sequencing is carried out on the DNA generated in (509).
511: Sequencing results are retrieved from (510).

Figure 6:
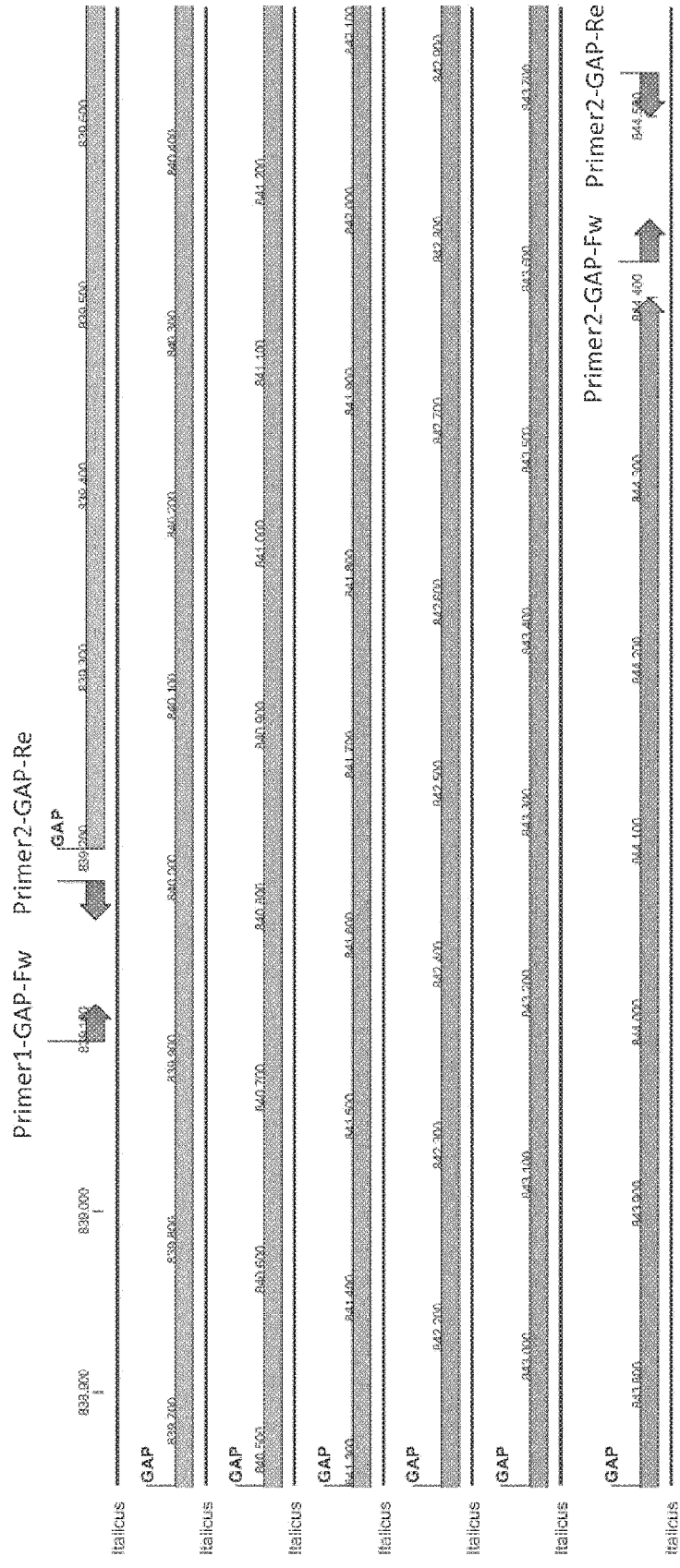

FIG. 6: A schematic illustration of primers and gaps used for GAP-closing.
The horizontal black line illustrates a DNA sequence of 5712 bp. GAP illustrates the desired sequence where sequence data could not be obtained from the paired end library. Primers are placed on both sides of the gap, and each set is placed in close proximity to the GAP. Primers are designed to target DNA and generate fragments of 50-100 bp.

Figure 7:
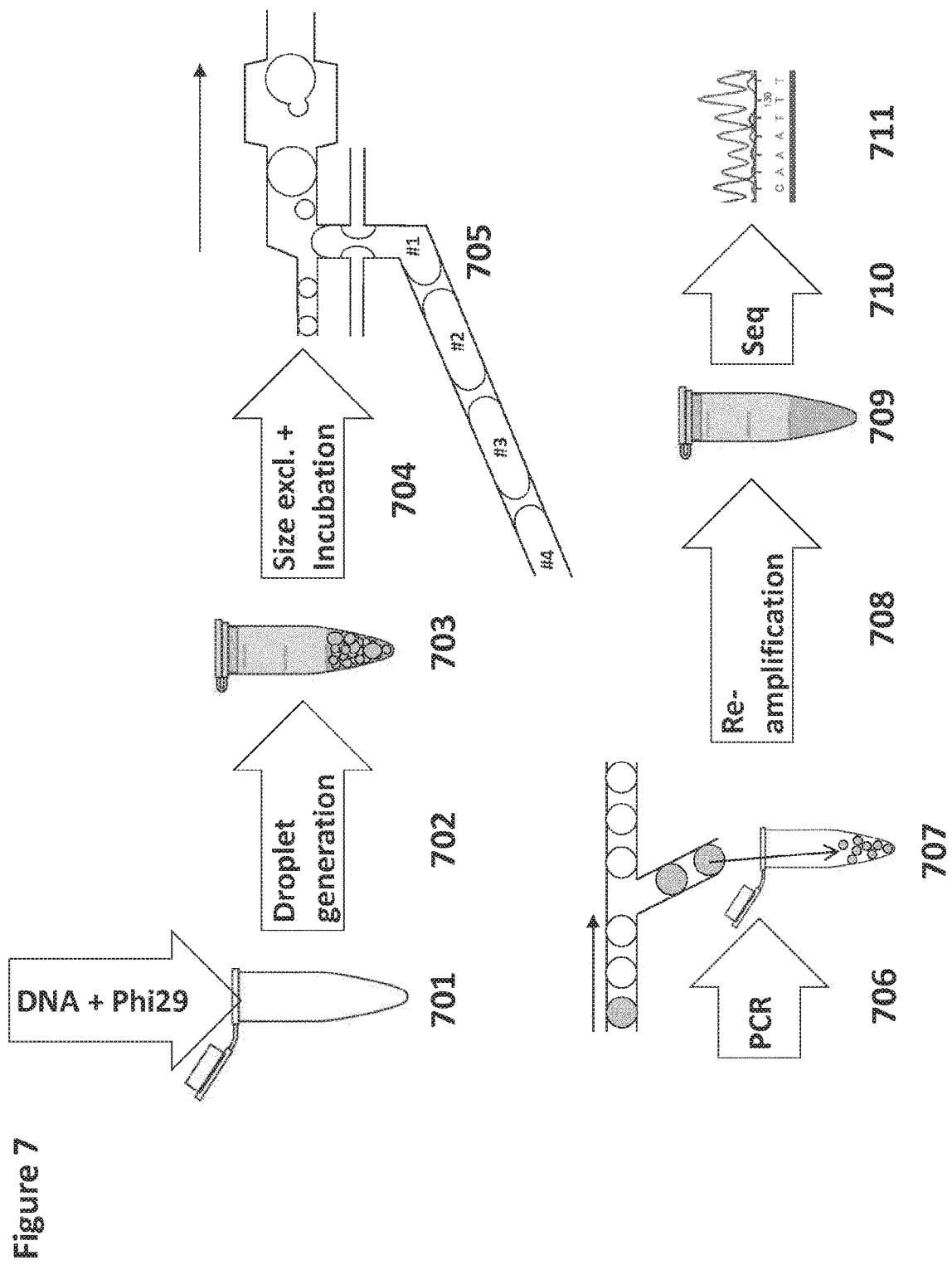

FIG. 7: Outline of a scheme for performing NEEDLS as described in example 2.
701: DNA, reagents for general amplification, and droplet oil are mixed.
702: Vortex is applied to mix liquids and to generate droplets of variable sizes.
703: Droplets are incubated.
704: Large droplets are excluded and discarded.
705: Droplets are merged with dUTP mixtures wherein a subset of primers are present. #1-#4 is included in the figure for illustration purpose, whereas 10 different mixtures are included in the example.
706: PCR is performed.
707: Droplets where a positive PCR reaction is observed are sorted from the mixture. Droplet oil is removed by sonication followed by DNA purification. UDG treatment is applied to break down all uracil containing DNA. The DNA content is then purified by ethanol precipitation.
708: Re-amplification of the eluted DNA is carried out to ensure a sufficient quantity of DNA for nucleotide sequencing (e.g. NGS).
709: The amplified DNA is prepared for sequencing.
710: The complete mixture is sequenced and results are prepared for assembly.
711: Alignments of the received sequence is used to close gaps of the genome sequence.

Figure 8:
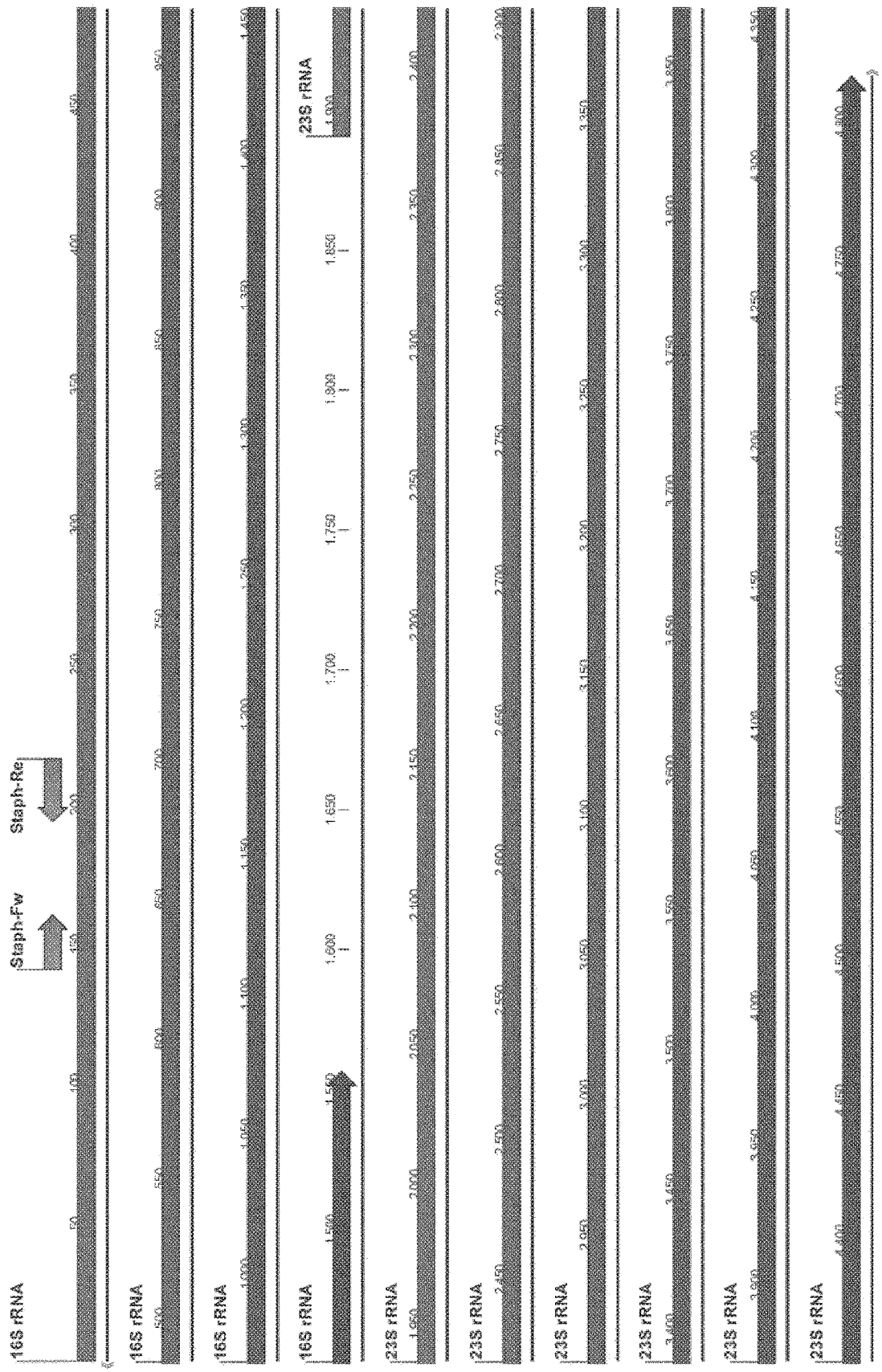

FIG. 8: Target DNA fragment identified by NEEDLS comprising sequence of 16S rRNA and 23S rRNA genes assigned to *Staphylococcus* genus [SEQ ID No. 10]

DETAILED DESCRIPTION OF THE INVENTION

The present invention pertains to an in vitro method in which the concentration of a specific target DNA molecule is increased relative to the concentration of total DNA in a sample, by 1) dilution of a sample into multiple sub-compartments such as droplets (separation), 2) non-specifically amplifying DNA within the droplets (general amplification), 3) addition of reagents for specific detection of the target sequence to the droplets, 4) detection of the specific target sequence within the droplets and, 5) physical selection of droplets containing the target sequence (selection).

The invention is based on the principle that, if only a fraction of the droplets contain the target sequence, the concentration of the target relative to total DNA is higher in these droplets, compared to the concentration in the original sample. The fraction of droplets containing the target determines the degree of enrichment; if the fraction is low, the enrichment is high.

In the context of the present invention, the presence or absence of the target DNA molecule in a sample of total DNA or a dilution thereof or droplet, is defined by the presence of detectable target DNA molecule in the sample or a dilution thereof or droplet using the selected method of detection (e.g. PCR).

The target can be further enriched by further rounds of selection (as above), until it can be sequenced by standard methods such as Sanger sequencing or Pyro sequencing or similar detection of DNA sequence or by PCR, hybridization or other detection assays, or it can be used directly from the first round of selection.

Droplets amplified and sorted according to the invention contain DNA fragments of 5-100 kb containing the DNA sequence used for detection and identification.

Surprisingly little prior DNA sequence information is needed for the enrichment according to the invention. In comparison to current enrichment technologies, only approximately 40 nucleotide base pairs of specific target information is required as compared to at least 5-8000 and 300 base pairs respectively for hybridization based and long range PCR based methods respectively (FIG. 1). It is known in the art, that the most sensitive PCR reactions are obtained when the fragment is short, such as 100-250 base pairs. Therefore, long range PCR, designed to amplify DNA fragments that are longer than 250 base pairs, for example 500 to 5000 base pairs in length, may not be applicable when the sample contains high amounts of background DNA. Also, hybridization based methods require the sample to be relatively pure to avoid non-specific hybridization. The only way to obtain sequence information from a mixed sample may therefore be sequencing of the entire DNA sample by e.g. next generation sequencing methods, and, although the cost of next generation sequencing is rapidly decreasing, the cost of sequencing thousands of genomes is still high.

The method of the invention is surprisingly efficient, whereby the extent of DNA sequencing can be reduced by a factor of more than 1 billion for 5 multiplexed DNA targets by three rounds of NEEDLS or a factor of 25 million for one target sequence using two rounds of NEEDLS (FIG. 2).

I: Droplet Exclusion Enrichment of Nucleotide Sequences

The essential steps of the NEEDLS method are further described below:

a) Providing a DNA sample comprising one or more specific target DNA molecule and reagents for general amplification of DNA (401)

A sample of mixed DNA molecules (i.e. a mixed population of DNA molecules) known to comprise a target DNA molecule, is selected for performing NEEDLS. One or more unique nucleotide sequences of at least 10 (or 15) nucleotides located within the target DNA molecule is selected for screening and detecting the DNA molecule by a desired method, such as PCR detection, DNA detection with hybridization probes or similar. A target DNA molecule may contain more than one unique nucleotide sequences, each sequence corresponding to a given genetic marker, for example a first genetic marker sequence diagnostic of an infectious agent and a second genetic marker diagnostic of an antibiotic resistance gene. Typically, the frequency of the target DNA molecule in the sample of mixed DNA molecules is less than $10^{-2}$, it may for example lie between $10^{-3}$ and $10^{-9}$ (calculated as base pairs of target sequence divided by base pairs of total DNA in the sample). Prior to amplification, the liquid sample of mixed DNA molecules is serially diluted by a desired number of dilutions until each droplet that is generated and processed in the subsequent droplet formation step contains mixed DNA molecules but contains less than 0.5 target DNA molecule on average, preferably less than 0.25 or even more preferably less than 0.1 specific target DNA molecule on average. Thus, if the liquid sample of mixed DNA molecules is separated into 100 droplets, each containing mixed DNA molecules, then on average the target DNA molecule will be present in less than 50 of these droplets, preferably less than 25 of these droplets, even more preferably less than 10 of these droplets. The presence or absence of the target DNA molecule in a droplet is defined herein as the presence or absence of detectable target DNA molecule when employing methods for specific detection of the target DNA molecule, such as those exemplified in the present application. This dilution is performed to ensure target enrichment; if the average number of droplets containing target is low, the frequency of target relative to non-target molecules within the droplet is high. The frequency and abundance of the target DNA molecule in the mixed DNA sample may be determined by PCR, real time PCR, by hybridization based assays or by assays detecting an RNA or protein product of the target sequence.

b) Formation of a multiple of droplets containing said DNA sample (403),

Droplets containing diluted sample mixed DNA molecules and reagents necessary for general amplification of DNA are generated using any method of droplet generation to isolate target DNA sequences in closed compartments. Suitable methods for droplet generation include active methods such as acoustic energy ejected droplets, dielectrophoresis (DEP) and electrowetting on dielectric (EWOD), and passive methods such as T-junction and flow focusing [1]. In addition to droplets, the general amplification can occur in other micro-volume compartments, such as reaction chambers in microfluidic chips.

c) General amplification of DNA molecules in a multiple of droplets each containing mixed DNA molecules and less than 0.5, preferably less than 0.25 or even more preferably less than 0.1 specific target DNA molecule on average (404)

DNA in each droplet is amplified using any method of total DNA amplification to increase the abundance of the DNA in each sample. Suitable amplification methods including Degenerate Oligonucleotide Primed PCR (DOP-PCR), Multiple Displacement Amplification (MDA)[4], randomly primed PCR or similar.

d) Specific detection of droplets containing said specific target DNA (405)

Following general amplification of total DNA in step c) the droplets are screened for the presence of the target DNA molecule using the desired detection technique. In at least one or more screened droplets that are shown to contain the target DNA molecule, the frequency of the target DNA molecule will be increased compared to its frequency in the sample of mixed DNA molecules in step (a). The increase in frequency is typically between 0.1×(number of droplets without target)×(number of droplets with target)$^{-1}$ and 10×(number of droplets without target)×(number of droplets with target)$^{-1}$. Alternatively, increase in frequency is calculated to lie between 0.1×(number of droplets without target)×(total number of DNA containing droplets)$^{-1}$ and 10×(number of droplets without target)×(total number of DNA containing droplets)$^{-1}$. The number of droplets containing target is typically between 2 and 100 per target sequence. The total number of droplets is at least 1,000, but typically greater than 10,000.

The presence of the target DNA molecule in the droplets may be determined by PCR including qPCR, by hybridization based assays or by assays detecting an RNA or protein product of the target sequence. The reagents for specific detection may contain dUTP to make it possible to selectively inactivate, degrade or remove the DNA amplified in the detection step using UDG, in a subsequent step.

e) Physical selection of droplets containing said specific target DNA (406)

Based on the detection of target DNA in step d) droplets are sorted into at least two different streams. When more than one specific target is detected in step d), the droplets may be sorted into 3, 4, 5 or more streams. In the stream containing droplets wherein the target DNA is detected, the abundance of the target DNA relative to non-target DNA in the droplets is enriched as compared to the sample of mixed DNA molecules in step a).

Optional steps:

f) inactivating, degrading or removing DNA produced for specific detection of target DNA When the enriched target DNA is used for further rounds of NEEDLS or other applications where the presence of the detection product interferes with these further processing, the amplification of DNA in the detection step c) can be performed using dUTP in place of one of the deoxyribonucleotide (dNTPs), where the product may then be optionally selectively degraded, inactivated or removed. This inactivation may be performed using an enzyme such as Uracil-DNA glycosylase, also known as UNG or UDG.

g) Repeating steps (a) to (e)
Using the droplets containing enriched target DNA obtained in (e) in a new step (a), the target DNA may be further enriched.

h) Amplifying the enriched sample
Using the droplets containing enriched target DNA obtained in (d), the target DNA may be further amplified using a general amplification such as MDA or a specific amplification such as PCR.

Scheme for Performing NEEDLS

The scheme is outlined in FIG. 4. (401) Determine the concentration of target DNA molecules in the original DNA sample of mixed DNA molecules. Dilute the sample until the expected average number of droplets containing a target molecule (positive droplets) is less than 0.5. If the abundance of only one target is enriched relative to non-target DNA in a droplet, the average number of positive droplets should be smaller resulting in a greater enrichment. Ideally, the entire sample of droplets should contain 2-100 positive droplets per target preferably 3-50 and more preferably 5-20. If more than one sequence variant of the target may be present, each variant counts as a separate target DNA molecule. The correlation between number of targets, the average number of positive droplets and the resulting enrichment after NEEDLS is shown in FIG. 3 using an example of one round of NEEDLS, 20,000 droplets and 10 positive droplets per target.

The observed enrichment may be higher than the expected enrichment of FIG. 3, as each of the positive droplets may contain different amounts of DNA amplified in the general amplification due to bias of this amplification step. In our experience the resulting enrichment may be at least two fold higher. Also, if smaller droplets are used such that more separate compartments are obtained, this will result in a greater enrichment.

Add reagents for multiple displacement amplification (MDA) to the diluted original sample; denature the DNA, anneal primers, and add the DNA polymerase for general amplification (e.g. φ29 DNA polymerase). Following the addition of the polymerase, generate droplets containing the MDA-ready sample in order to isolate the target molecules in separate compartments (403). Then, amplify the targets within the droplets by incubating the samples under conditions suitable for MDA (404).

Add reagents for detection to the droplets in order to allow detection of the target sequences or target sequences in the sample. These may be added either together with the reagents for general amplification (401) or after general amplification (between 404 and 405). If detection is performed using PCR; transfer the amplified droplet sample to a PCR unit and perform PCR amplification and then sort the droplets according to the presence (positive) or absence (negative) of the target molecule. Where fluorescent labelled PCR primers are used, the presence of the target molecule can be detected by the fluorescence of the samples using a fluorescence-activated droplet sorter (405 and 406).

Some positive droplets will give a higher fluorescence. When using a cut-off value to select the droplets with the highest fluorescence, this will select for droplets having a correspondingly greater enrichment. Determine the abundance of the target DNA molecule, and if this is sufficient for analysis methods, such as sequencing, the selected sample may be analysed directly; otherwise additional rounds of NEEDLS can be applied.

When it is necessary to perform further rounds of enrichment, it may be preferred to degrade or remove the DNA generated in the detection step. It may be preferred to use dUTP in the PCR reagents. The MDA reaction is then performed using standard dNTPs. After detection and physical selection of droplets, the DNA generated in the PCR can be degraded and the treated sample can be used for an additional round of enrichment, starting with dilution and multiple displacement amplification in droplets.

When a sufficient enrichment is reached using NEEDLS, the droplets are coalesced. The enriched DNA in the coalesced droplets may also be further purified and may be further amplified using general or specific amplification such as MDA and PCR respectively.

II: Multiplex NEEDLS

NEEDLS can be adapted to perform multiplex NEEDLS. Multiplex NEEDLS employs additional features that are designed to detect a 2nd consecutive sequence of at least 10 (or 15) nucleotides in the sample of mixed DNA molecules analysed, by amplification of this 2nd consecutive sequence with sequence specific primers to generate a 2nd target DNA molecule. If several droplets show specific detection (e.g. by fluorescence signal) from both the 1st and 2nd consecutive sequence then they must be located on the same MDA-amplified target DNA molecule. Similarly, it is envisaged that the unique sequence of from 1 to 20 or more different specific target DNA molecules can be detected in a mixed sample of DNA molecules, using the method of the invention, by employing specific primers to detect each of the different specific target DNA molecules.

Accordingly, in addition to providing information concerning co-localisation of targets, multiplex NEEDLS provides simultaneous purification of up to thousands of different target molecule, each comprising more than 5,000 base pairs. Separate detection molecules can be provided to separate droplets or can be added as a mixture.

III Samples Analysed by NEEDLS and Multiplex NEEDLS

III.i Sample of Mixed DNA Molecules

NEEDLS may be applied to a sample of mixed DNA molecules known to comprise a target DNA molecule. A sample of mixed DNA molecules comprises a population of DNA molecules (e.g. chromosomal DNA molecules or plasmid DNA molecules) where the individual DNA molecules within the population differ by at least one nucleotide within a known consecutive sequence of at least 10 (or 15) nucleic acid base pairs in their DNA, such that a target molecule comprising the known consecutive sequence differs from, and can be distinguished from, non-target molecules in the sample. The sample of mixed DNA molecules may additionally comprise single stranded RNA or DNA polynucleotides. The population of DNA molecules in the sample of mixed DNA molecules comprises the target DNA molecule.

The target DNA molecule can be in linear or circular forms. Circular DNA can occur naturally or can be obtained by cloning DNA into plasmids, fosmids, cosmids, BAC clones, or generated by ligation or through Cre/LoxP mediated recombination.

A target DNA molecule comprises one or more known unique consecutive sequence of at least 10 (or 15) nucleic acid base pairs (or nucleotides). A target DNA molecule can be selected from a sample of mixed DNA molecules, by selecting for a target DNA molecule comprising this unique consecutive sequence of at least 10 nucleic acid base pairs (or nucleotides). The target DNA molecule can also be selected from the sample of mixed DNA molecules, by selecting for a target DNA molecule comprising at least two unique consecutive sequences of at least 10 (or 15) nucleic acid base pairs (or nucleotides), wherein the two consecutive sequences are comprised within a DNA molecule of 50 to 100,000 nucleic acid base pairs, preferably 150 to 3,000 nucleic acid base pairs, more preferably 150 to 1500 nucleic acid base pairs.

Typically, the frequency of the target DNA molecule in the sample of mixed DNA molecules is less than $10^{-2}$, it may for example lie between $10^{-3}$ and $10^{-9}$ (calculated as base pairs of target sequence divided by base pairs of total DNA in the sample).

The method of the invention is particularly suitable where the frequency of the target DNA molecule in the sample of mixed DNA molecules is less than $10^{-2}$. The method of the invention is also suitable where the frequency of the target DNA molecule in the sample of mixed DNA molecules is $10^{-4}$, $10^{-5}$, $10^{-6}$, $10^{-7}$, $10^{-8}$, $10^{-9}$, $10^{-10}$, $10^{-11}$, or lower. In many instances, the sample of mixed DNA molecules will be derived from a cell population comprising genomic DNA, while in other instances, the sample may be derived from samples where the DNA molecules are of diverse origin, such as samples collected from nature. Irrespective of its source, the frequency of the target DNA molecule is defined as the number of specific target DNA base pairs divided by the number of total base pairs in the sample. The frequency of the target DNA molecule in the sample of mixed DNA molecules is determined by making a dilution series in triplicate, detecting the presence or absence of target and determining the number of targets using, for instance, most probable number methods. The frequency of the target molecule can also be determined using qPCR or digital droplet PCR [2]. The concentration of DNA is measured and the number of total genome equivalents is determined by dividing this concentration by the average molecular weight of the genome.

III.ii Source of the Sample of Mixed DNA Molecules

According to one embodiment of the present invention, the target DNA molecule is derived from the genome of a cell, where the genome may be either chromosomal or extra-chromosomal DNA. Further, the target DNA molecule may be derived from a cell, where the cell is selected from amongst a microbial cell, a plant cell, an animal cell, or a mammalian cell. The mammalian cell may be a human cell. The microbial cell may be a bacterial cell, a yeast cell or a fungal cell. Furthermore, the target DNA molecule may be derived from a fungal mycelium or fungal spores.

When the target DNA molecule is derived from one or more cell, the cell(s) may be part of a multicellular tissue or multicellular organism.

Furthermore, the target DNA molecule may be derived from one or more viral particles, where the virus has an RNA or DNA genome. Alternatively the target DNA molecule may be derived from a host genome comprising integrated DNA derived from a virus. The target DNA molecule may also be derived from a bacteriophage.

Irrespective of the derivation of the target DNA or RNA molecule, the target DNA or RNA molecule is present in a sample of mixed DNA molecules, where the mixed DNA molecules may be derived from a sample collected from nature, for example a sample of soil, water or air. Alternatively, the sample may be derived from a multicellular organism, such as a mammal, for example an animal or a human subject. When the sample is derived from a mammal, the sample (for example a biopsy) may be derived from a body fluid (e.g. blood, plasma, serum, lymph and urine), from faeces or from a body tissue or organ. The multicellular organism from which the sample is derived may be a living or may be a dead organism.

III.iii Preparation of the Sample of Mixed DNA Molecules

The sample of mixed DNA molecules comprising the target DNA molecule may be prepared from a sample collected from nature or from an organism (e.g. a biopsy). Methods for selective extraction of DNA molecules are known in the art [3]. When the target DNA molecule is derived from a cell, the step of cell disruption or cell permeabilisation is normally required in order to release total nucleic acid molecules (including DNA or RNA) from a cell, this step preceding the subsequent step of selective extraction of DNA molecules.

Where the target DNA molecule is derived from an RNA genome, the RNA genome or parts thereof are first reverse transcribed to provide a cDNA molecule, where the nucleotide sequence of the cDNA corresponds to (is a reverse transcript of) the RNA genome.

III.iv Generation of Droplets

Methods of the invention include forming multiple sample droplets where the droplets each contain less than 0.5 specific target molecule on average. In the preferred embodiment the distribution of specific target molecules follows Poisson distribution. Some droplets may contain non-target molecules present at 10 fold or higher concentrations as compared to the target molecule, while other droplets may contain only the target molecule.

Generally, droplets can be formed by a variety of techniques such as those described in [4-6]. Methods of the invention may involve forming a two phase system comprising aqueous droplets surrounded by an immiscible carrier fluid. In a preferred embodiment, the aqueous sample within the droplet is prepared by preparing a mixture containing sample DNA, primers such as random hexamer primers and buffer solutions. The DNA mixture is subjected to conditions resulting in denaturing of the DNA such as temperatures of around 94° C. for 1-10 minutes. The mixture is rapidly cooled and added to a mixture containing dNTPs and a polymerase useful for general amplification, such as Phi29 polymerase. The resulting mixture is used as the aqueous sample in two-phase liquid droplet formation using two immiscible liquid phases. Aqueous droplets are either generated in an apparatus having means for creating a vortex/turbulence in a sample comprising two immiscible liquid phases in controlled environments, creating droplets of liquid (phase 1) in a 2nd phase liquid by controlling the mechanical parameters and thereby also the liquid volume of each generated droplet or by a means for extruding droplets of one liquid phase in a 2nd immiscible liquid phase, where the so formed droplets remain discrete and wherein the volume of the droplet is controlled by the diameter of the means for droplet extrusion.

The carrier fluid is one that is immiscible with the sample fluid. The carrier fluid can be a non-polar solvent, decane, fluorocarbon oil, silicone oil or any other oil (for example mineral oil).

In certain embodiments, the carrier fluid contains one or more additives such as agents which increase, reduce, or otherwise create non-Newtonian surface tensions (surfactants) and/or stabilize droplets against spontaneous coalescence or contact.

IV Methods of General Amplification of DNA Suitable for NEEDLS

A range of different approaches have been suggested for general amplification of DNA, such as randomly degenerate primed PCR, linker ligation PCR, or, Degenerate Oligonucleotide Primed (DOP) PCR and Multiple Displacement Amplification (MDA). MDA has proven efficient in performing whole-genome amplification (WGA) of even very small amounts of DNA [7]. Compared with more traditional PCR-based WGA methods, MDA generates DNA molecules with a higher molecular weight, having better genome coverage. MDA employs a strand displacement polymerase that possesses two enzymatic activities: DNA synthesis (polymerase) and an exonucleolytic activity that degrades single stranded DNA in the 3'- to 5'-direction, as exemplified by bacteriophage phi29 DNA polymerase, that belongs to eukaryotic B-type DNA polymerases (UniProtKB/TrEMBL: Q38545). Other useful polymerases include BstI polymerase.

To obtain the enrichment according to the invention, general amplification is performed within droplets. The droplets serve to isolate target molecules into compartments separate from compartments not containing target DNA. Amplification is performed in each droplet for example by using any of the above listed general DNA amplification methods. In some embodiments, the amplification is performed at around 30° C. for one hour, preferably for less than 30 minutes.

V Methods of Adding Detection Reagents to Droplets

Following general amplification, reagents for detection of target DNA molecules may be added to the droplets. Alternatively, the reagents for detection may be added before droplet generation. Addition of reagents to droplets may be performed using an apparatus with means for providing aliquots of an aqueous liquid (e.g. comprising PCR reaction or other detection mixture), and means for fusing said aliquots with droplets of an aqueous liquid that are suspended in a 2nd immiscible liquid (e.g. droplets from general amplification step), and means for delivering said fused liquid droplets suspended in a 2nd immiscible liquid to a further compartment. Examples of droplet fusion or droplet injection techniques are described in [5, 8]. In certain embodiments of the invention, the reagents added to the droplets containing generally amplified DNA comprise specific primers or a specific probe complementary to the specific target DNA to be detected. When specific primers are added, the reagents comprise a DNA polymerase such as Taq polymerase and dNTPs. In addition, the reagents may contain dUTP, to enable subsequent degradation of DNA generated in the detection step, and/or a nucleic acid dye enabling detection based on fluorescence. In other embodiments the detection is based on fluorescence from labelled probes or primers.

VI Methods of Detecting the Target Sequence

Methods of the invention further involve detection of the target nucleic acid molecule within the droplets containing DNA amplified using general amplification. In certain embodiments the detection involves amplification of a part of the target molecule. The amplification reaction, that is suitable for amplifying nucleic acid molecules, includes the polymerase chain reaction, or nested polymerase chain reaction including or excluding probes such as Taqman probes, Scorpion probes, Molecular Beacon probes, and any other probe that functions by sequence specific recognition of target DNA by hybridization and result in increased fluorescence on amplification of the target sequence. Methods according to the invention also include methods wherein detection is based on fluorescence from optically labelled probes such as fluorescently labelled probes wherein the target is not amplified after general amplification. In this case, the DNA is denatured e.g. by increasing the temperature to around 95° C. and the probe is subsequently allowed to anneal to the target, resulting in activation of the probe or probes. Such optically labelled probes can be Molecular Beacons, where a single-stranded bi-labeled fluorescent probe is held in a hairpin-loop conformation of around 20 to 25 nt by a complementary stem sequences of around 4 to 6 nt. Due to the loop-structure the desired fluorochrome attached to one end of the sequence is in close proximity of the light quencher attached to the other end. When the structure is released during denaturing and then re-annealed, the probe anneals to an amplified target. When annealed, the hairpin structure is no longer maintained, and the quencher no longer quenches emitted light from the fluorochrome. The optically labelled probes can also be FRET (fluorescence resonance energy transfer) probes.

VII Methods of Physically Selecting Droplets Based on Presence of the Target Sequence To selectively separate droplets comprising a detectable target DNA molecule from droplets wherein the target is not detected, a variety of different methods for physical selection of droplets or droplet sorting can be employed including steering, heating, and acoustic waves [5]. Such physical selection can be carried out using an apparatus with means for receiving droplets of an aqueous liquid that are suspended in a 2nd immiscible liquid (e.g. droplets from specific detection step), and means for passing each droplet past a detection unit capable of detecting a detectable component in said droplet, and means for addressing said droplet for delivery to a selected compartment as determined by the presence or absence of the detectable component and means for delivering said droplet to the selected compartment.

VIII Methods of Removing the Detection Signal Molecules after Physically Selecting the Droplets After physically selecting the droplets based on the presence of the specific target sequence, it may in some cases be necessary to remove a detection signal, such as a PCR product. Several methods for removing such signals are known in the art. If dUTP has been used in the detection reaction, the detection molecule may be removed using uracil-DNA N-glycosylase [9]. Alternatively, as the molecules produced by general amplification are significantly longer than the detection molecules, the detection molecules can be separated using methods based on size separation such as size exclusion based on differential binding affinity of small and large DNA to silica particles [10]. Such silica surfaces have limited binding efficiency to DNA fragments smaller than 100 bp, and consequently only DNA fragments smaller than 100 bp will be efficiently discarded, when silica based purification in applied. In some applications, however, it may not be necessary to remove the detection molecule. For instance, since Phi29 and some other polymerases have low activity on DNA molecules shorter than 1000 base pairs, it may not be necessary to remove the detection molecule if the step following NEEDLS enrichment is a general amplification, since the detection molecule will only be amplified to a limited extent, if at all amplified, compared to the actual targeted larger DNA molecule.

IX Sequence Determination of the Target DNA Molecule

Enrichment of the target DNA molecule by NEEDLS is based on detection of one or more unique consecutive sequence of at least 15 nucleotides in said DNA molecule. When detection is based on PCR, where the one or more unique consecutive sequences are amplified to generate a target DNA molecule, the nucleotide sequence of this molecule can be determined. In addition, the nucleotide sequences flanking the target DNA molecule in the 5' and 3' direction can be determined by rapid genome walking (RGW)[11]. RGW is a simple, PCR-based method for determining sequences upstream or downstream in a larger DNA molecule starting from a known sequence, such as a target DNA molecule. RGW enables individual amplification of up to 6 kb in a large DNA molecule using PCR. The sequences can be extended simply by performing multiple cycles of RGW, using new primers based on the sequence obtained in previous cycles. Typically libraries are constructed from a purified sample of the large target DNA molecule, by digesting the DNA separately with four different restriction enzymes and ligating the products to a specially designed adaptor. The ligated DNA is then sequenced with primers annealing to the adaptors or to known sequences within the DNA, using the desired DNA sequencing method, such as Sanger sequencing, pyro sequencing, sequencing by synthesis, ligation or two base-coding sequencing or similar methods [12].

The enriched target DNA sequence can also be sequenced using e.g. Sanger sequencing, Emulsion PCR, Shotgun sequencing, SOLID sequencing, bridge PCR, Ion Torrent sequencing, Polony sequencing, Pyrosequencing, Sequencing by synthesis, DNA nanoball sequencing, Heliscope single molecule sequencing, Nanopore DNA sequencing, Tunnelling currents DNA sequencing, Sequencing by hybridization, Sequencing with mass spectrometry, Transmission electron microscopy DNA sequencing, RNAP (RNA Polymerase) sequencing or Single-molecule real-time sequencing.

IX.i Research and Development Applications of NEEDLS

Use of NEEDLS to isolate or enrich target DNA in a mixed sample of DNA molecules extracted from samples collected from nature, or from clinical samples provides direct access to the genome, or parts thereof, that cannot be analysed by other methods because of the sample complexity. NEEDLS is particularly useful for isolating or enriching DNA molecules involved in hereditary diseases, cancer, and infectious diseases.

Multiplex NEEDLS is particularly useful for simultaneous isolation or enrichment of more than one target DNA from samples comprising several target DNA sequences, such as a sample to be analysed for the DNA sequence of more than one virus, more than one hereditary disease or more than one cancer related gene.

NEEDLS is also particularly useful for obtaining target DNA sequence information from samples where only a small part of the sequence is known prior to enrichment, since the technique only requires a small part of the target DNA sequence to be known in order to perform the detection step and furthermore takes advantage of the high fidelity of polymerases (like Phi29) in the MDA amplification to generate large amplified DNA molecules of up to 100,000 bp.

IX.ii Sample Preparation for Sequencing

When performing sequencing of large DNA molecules such as genomes, the sequence information obtained will often contain gaps where the sequenced molecules do not overlap or cannot be assembled. NEEDLS is particularly useful for gap closing of DNA sequences, as NEEDLS will retrieve up to 100,000 bp of sequence surrounding the small detection area and can therefore be designed to cover the unknown gap region.

NEEDLS is also particularly useful when sequencing samples containing more than one variant of a target DNA sequence such as chromosomal DNA containing two alleles of a gene. In this case, droplets containing each detection sequence are collected in separate compartments to ensure that only one copy of the sequence is present. The droplet may subsequently be barcoded separately to enable the separate sequencing of each variant of the target DNA sequence.

IX.iii Diagnostic Applications of NEEDLS

NEEDLS may be used to analyse target DNA in samples derived from multicellular organisms, such as a biopsy or a sample of body fluid or faeces obtained from a subject (e.g. human or animal subject), for the diagnosis or monitoring the progress of a medical indication or disease.

Diagnosis of a wide range of medical indications in a subject such as a disease caused by an infectious agent (e.g. micro-organism or virus) can be assisted by the isolation or enrichment and detection of a target DNA or RNA molecule that is derived from the genome of the infectious agent by NEEDLS or Multiplex NEEDLS, where the target DNA molecule is detected in a sample of mixed DNA molecules derived from a biopsy or sample of body fluid obtained from a patient.

Use of NEEDLS in target DNA molecule isolation provides the additional feature, that additional diagnostic features of the disease can be determined. For example, where the genome of the infectious agent comprises resistance genes that confer resistance to certain therapeutic agents, enrichment of a resistance gene may also retrieve the region surrounding the resistance gene and may provide information about the specific infectious agent carrying the resistance.

NEEDLS may be applied to diagnostics such as detection of presence of an infectious agent such as a prokaryotic organism and antibiotic resistance. Such cases can be the presence of methicillin resistance (MR) in *Staphylococcus aureus* (SA). The combination of (MRSA) is a well-known problem in hospitals and similar facilities, whereas MR may not cause comparable problems if it is not present in SA. NEEDLS can be used for detection of co-existence of MR and SA if a method such as duplex detection is applied. Such duplex detection can be a dual-reporter detection system, where one detection system is used to monitor the presence of one event such as MR whereas another detection system is used to monitor the presence of another event, such as presence of SA within the same droplet. When both MR and SA are present in the same droplet, the two loci are likely to be localized on the same DNA fragment. Moreover, NEEDLS can be applied to selectively retrieve additional DNA sequences from the host genome based on the presence of genes such as MR or SA. Thus, it can be used to provide additional sequence information from the genome of the infectious organism.

NEEDLS may also be used to assist diagnosis of a disease caused by, or originating from the presence of a viral agent in a subject. Using multiplex NEEDLS, the presence or absence of viral DNA at a known integration site can be determined by tracking the co-enrichment of the viral DNA and integration site DNA sequence.

NEEDLS may be applied to multiple genes within a single genome or within multiple genomes, which may be detected by any suitable molecular detection method. If required, a series of multiplex PCR reactions can be carried out and differentiated using specific dyes for each reaction. This can be done by introduction of detection systems such as probes such as Taqman probes, Scorpion probes, Molecular Beacon probes or similar. Moreover, NEEDLS can also be applied to a series of genes which are not necessarily differentiated at the point of detection. Differentiation can be applied after sequence retrieval, using such methods as bar-coded PCR or similar.

X NEEDLS and Bias in Amplification

NEEDLS is based on specifically selecting samples where amplification of a desired DNA region from a complex, mixed DNA sample has occurred. Although Phi29 based amplification (MDA) has been described repeatedly as the most reliable genome amplification currently available, it is known to introduce significant bias. Pan et al. [18] states in general terms that a highly specific whole genome amplification (WGA) of complex DNA pools which avoids amplification bias remains a challenge. Moreover, similar observations are seen with alternative amplification methods such as DOP-PCR and random priming PCR. These two amplification methods are described as being much less efficient at reproducing the locus representation [19], resulting in even more biased amplification products. While bias is seemingly unavoidable, regardless of the amount of reaction template [20] present, the amount of template independent product (TIP) or bias introduced during amplification is seemingly correlated negatively to the amount of DNA template in the reaction and has in some studies been documented to represent 70-75% of the total yield [18]. Whole genome amplification is applied to amplify DNA in the NEEDLS process and it would therefore be expected that these general challenges relating to bias in genome amplifications would also apply to NEEDLS. As a procedure including WGA it would thus be expected that significant bias against the target DNA molecule should be observed. Hence a procedure such as NEEDLS employing WGA would not have been considered as a method capable of enriching for a specific region of DNA in a mixed sample.

Surprisingly, the challenge of TIP/bias is not seen when applying the NEEDLS technique even though the initial concentration of the target DNA molecule is very low. The minimal negative TIP/bias observed in the NEEDLS system is significantly lower than the overall gain obtained from the amplification process and the net result is therefore a substantial enrichment of the target DNA molecule.

The method does not require a dilute initial DNA template, as high concentrations of DNA also can efficiently be subjected to NEEDLS. In this case only a few fold of amplification by the WGA method is needed.

XI NEEDLS Reduces Analytical Burden

NEEDLS provides a highly efficient analytical tool for detecting and characterising a DNA target in a large genome of a biological sample, for example the human genome of a biopsy. This can be illustrated with the following example:

The analytical task is to detect and determine the nucleotide sequence of a target DNA molecule in a sample of mixed DNA fragments comprising 100,000 DNA molecules with an average size of 30 kb, wherein 1 molecule is the target DNA. This sample of mixed DNA fragments corresponds to approximately 1 human genome of 3 billion base pairs with an average DNA fragment length of 30 kb. The nucleotide sequence of only 200 base pairs out of the 30 kb target DNA is known at the beginning of the analytical procedure.

When implementing the method of the present invention, then:

1. The DNA is aliquoted into droplets such that each droplet contains mixed DNA fragments, and such that there are 5 DNA fragments per droplet, on average. The number of droplets will therefore be 100,000/5=20,000 droplets. Only one of the 20,000 droplets will contain the target DNA molecule (thus, each droplet will contain less than 0.1 copy of the target DNA molecule).

2. The DNA in all droplets is then copied by general amplification resulting in 20,000 droplets containing amplified DNA, and the target DNA molecule is specifically detected in the same droplets (e.g. by PCR). The droplet containing target DNA is physically selected (sorted), and the DNA sequenced. Note that selection of the droplet comprising the one target DNA molecule, and (on average) 4 non-target DNA molecules, corresponds to an increase in frequency (enrichment) in the range of $2 \times 10^3$ and $100 \times 10^3$ [i.e. between $0.1 \times$(number of droplets without target)$\times$(number of droplets with target)$^{-1}$ and $10 \times$(number of droplets without target)$\times$(number of droplets with target)$^{-1}$].

3. Thus, when using the NEEDLS method of the invention, a total of 20,000 droplets must be prepared with amplification reagents (and detection reagents), and the detected droplet comprising the amplification product of the 5 DNA molecules (on average) each of 30 kb (on average) (=150,000 base pairs) must be individually sequenced in order to detect and analyse the 1 target DNA molecule.

When traditional methods for analysing mixed DNA samples are used for this analytical task, the analytical burden is many fold increased because the mixed DNA sample must first be converted into a library of cloned DNA fragments or amplified DNA fragments, where each member must be analysed, as illustrated by a classical protocol set out below:

1. The mixed DNA sample is aliquoted into droplets under conditions where the likelihood of a droplet containing 2 DNA molecules is low, e.g 0.1% corresponding to a statistically conservative probability of p=0.001 or less. The number of droplets required for this method is based on the number of DNA molecules and the probability of finding <1 molecule in an aliquot. This can be calculated (approximately) as the square root of the probability of finding 2 DNA molecules in the same droplet (i.e. 0.03162).

Since the mixture DNA sample has 100,000 DNA molecules, then a conservative estimate of the number of droplets required (to ensure that the likelihood of 2 DNA molecules in one droplet is statistically insignificant) is $100,000 \times 1/0.03162$ or $3.16 \times 10^6$ droplets ($0.03162 \times 0.03162 = 0.001$). The DNA in each droplet can then be either 1) copied by general amplification or cloning, and/or 2) the target DNA is specifically amplified by PCR.

2. All $3.16 \times 10^6$ droplets are then generally amplified; wherein 100,000 droplets will contain amplified DNA (of which 1 droplet will contain the target DNA). The 100,000 droplets comprising amplicons will be selected, and all 100,000 selected droplets must then be analysed in order to detect the target DNA molecule, since no enrichment of the target (increase in the target DNA/non-target DNA ratio) is achieved using this procedure.

If the $3.16 \times 10^6$ droplets are directly and specifically amplified using PCR with primers designed to amplify the known sequence of 200 base pairs (as the rest of the fragment is unknown it cannot be specifically amplified), then the 1 droplet containing target DNA may be detected and selected. However, here, only 200 base pairs out of the 30 kb have been amplified and its flanking sequences will remain unknown.

Accordingly, using this classical method, at least 3.16 million droplets must be prepared with amplification reagents, and the amplification product of at least 100,000 DNA-containing droplets must be screened by PCR individually in order to detect and to sequence the 1 target DNA molecule.

TABLE 1

| | Classical screening method | | Current invention |
|---|---|---|---|
| | General amplificication | Specific amplification | General amplification |
| Original sample | | | |
| Target DNA molecules @ 30 kb | 1 | 1 | 1 |
| Total DNA molecules @ 30 kb | 1.00E+05 | 1.00E+05 | 1.00E+05 |
| Target base pairs | 3.00E+04 | 3.00E+04 | 3.00E+04 |
| Total base pairs | 3.00E+09 | 3.00E+09 | 3.00E+09 |
| Ratio target to non-target | 1.00E−05 | 1.00E−05 | 1.00E−05 |
| Droplets | | | |
| # Total droplets | 3.16E+06 | 3.16E+06 | 2.00E+04 |
| # With non-target DNA | 1.00E+05 | 1.00E+05 | 2.00E+04 |
| # With target DNA | 1 | 1 | 1 |
| Fraction of partitions with more than one nucleic acid | Insignificant | Insignificant | High |
| After amplification | | | |
| Total droplets | 3.16E+06 | 3.16E+06 | 2.00E+04 |
| Droplets with amplified DNA | 1.00E+05 | 1 | 2.00E+04 |
| Droplets with amplified known part of target DNA | 1 | 1 | 1 |
| Droplets with generally amplified target DNA | 1 | 0 | 1 |
| After detection | | | |
| Droplets selected/sorted | 1.00E+05 | 1 | 1 |
| End result | | | |
| Amplified DNA (target bp) | 3.00E+04 | 200 | 3.00E+04 |
| Amplified DNA (bp total) | 3.00E+09 | 200 | 1.50E+05 |
| Ratio target to non-target | 1.00E−05 | Pure | 2.00E−01 |
| Enrichment | none | 200 bp fragments | 10000 fold |

EXAMPLES

Example 1. Complete Operon Coding for a Targeted Enzymatic Activity from a Compost Sample In this example it is demonstrated how a dual channel micro fluidics system can be applied to separate, amplify, identify, isolate, and re-amplify a targeted lipase DNA molecule. The targeted DNA including the adjacent DNA is made available for sequencing from the indigenous host. The procedure is shown schematically in FIG. 5.

DNA Extraction and Initial PCR

A mixed sample from a compost pile (core temperature 38° C.) was used for retrieval of the initial DNA sample. DNA was extracted from 5 gram sample using bead-beating as described elsewhere [13]. The extracted DNA was initially tested for presence of the targeted lipase gene, and was found to contain sufficient amounts of DNA for the applied PCR primers Lip-Fw: 5'-CTG AAT GGG GGA ATA ATG ACA AGC C-3' [SEQ ID 1] and Lip-Re: 5'-CTA TAC TCT TCT TTT AAT TCC TCA GC-3' [SEQ ID 2] to yield a PCR product of approximately 105 bp. PCR conditions were 94°, 62.1°, 72° (15 sec/15 sec/90 sec) for a total of 40 cycles.

Droplet MDA/Fusion/Sorting (Physical Selection)

A Phi29 reaction volume of 100 μL was created as described by Pan et al. [14]. While still keeping the reaction mixture cold (max. +4° C.), the Phi29 mixture was loaded into a well in an eight-channel disposable droplet generator cartridge (Bio-Rad). The same procedure was followed for additional wells, to use the full capacity of the droplet cartridge. Then, the remaining channels were filled with droplet oil (BioRad). The fully loaded droplet generator cartridge was then placed into the droplet generator (Bio-Rad) for droplet formation of the full reaction volumes in all reaction compartments of the cartridge (502).

After droplet formation had been completed, all droplets were manually transferred to a 1.5 ml Eppendorf collection tube, and the amplification reaction was thereafter placed in an Eppendorf Thermoshaker for 16 hours at 30° C. (504). Following incubation, the reaction was terminated by increasing the temperature to 65° C. for 10 minutes. The entire reaction volume (still in the form of separate droplets inside the Eppendorf-tube) was then transferred to the droplet-fusion-device (504) where the fusion of two separate streams were merged to generate fusion droplets each having a 10 times larger volume than the original SampliPhi droplets.

The volume increase was applied by merging the streams (Stream 1: SampliPhi-droplets where amplification had occurred & Stream2: dUTP-PCR where all the reactions components for PCR detection are present). By merging the two streams and carrying out the associated PCR reaction, it was enabled to monitor which merged droplets contained the desired target. Stream1 consisted of 1 nL individual droplets of the sampliPhi reaction mentioned above, whereas 9 nL droplets (stream 2) were formed from a mixture consisting of: 537 μL $H_2O$, 220 μL PCR buffer with Mg++(×5), 110 μL dNTP/dUTP mix (2 mM), 110 μL of each primer (10 pmol/μL), 110 μL BSA, 1 μL SybrGreen (1:10.000), 22 μL DreamTaq polymerase (5 U/μL).

The 10 fold volume surplus of dUTP-PCR was applied to ensure a proper dilution of MDA-components in order to avoid PCR inhibition during dUTP-PCR amplification and at the same time to establish a thorough detection basis in the following screening.

The fused droplets were collected in single PCR-tubes and were subjected to the same PCR conditions as described in the primary screening for target presence (506). After finalizing PCR, the 10-11 nL droplets were aligned in a separate micro fluidics chamber, and successfully amplified droplets were detected and selectively separated based on a 525 nm emission of fluorescent signal when excitated with a 488 nm laser beam (507).

A total of 16 droplets (out of 19.836) were detected as positive and were physically selected using a micro channel sorting cartridge combining all positive droplets in one chamber. The sorted droplets were manually transferred to a 1.5 ml Eppendorf-tupe, by adding 20 μL 5 mM Tris to the collection compartment of the micro channel sorting cartridge. Droplet immersion oil was removed by addition of SDS, and the amplified products were purified using ethanol precipitation. The purified products were re-suspended in 5 μL Nuclease free water.

The 5 μL volume of eluted dUTP-PCR products including the initial template was subjected to selective degradation using the Uracil-DNA Glycosylase (UDG) kit AmpErase® (Life Technologies) in a reaction volume of 25 μL, leaving only the initial template intact. Thereafter, the mixture was re-amplified using SampliPhi amplification (508) resulting in a final product concentration of 200 ng/μL in a total reaction volume of 20 μL.

PCR, identical to the initial screening, was used to verify the presence of the desired DNA target molecule, and RGW was used to obtain sequence from the gene and DNA in both 5' and 3' to the gene to describe the full gene, with promoter region, Shine-Dalgarno sequence and stop codon (510 and 511).

Example 2—Gap Closing of Genomes

This example describes how an unfinished genome sequence can be "gap-closed" using a single pass of NEEDLS by selectively choosing the regions of interest by traditional primer design. In this example, gap-closing is implemented on a paired end library which shows the presence of 57 gaps in the genome of *Thermoanaerobacter italicus* (CP001936). In the current example, gaps range in sizes from 422 bp to 5,201 bp. One single pass of NEEDLS followed by re-sequencing by Next Generation Sequencing (NGS) efficiently closes all gaps in the otherwise unfinished genome. The gaps are closed by specifically selecting and sequencing those droplets in which amplification of the desired regions have taken place. By doing so, a selectively targeted re-sequencing was accomplished, and all gaps were closed to generate a full circular genome.

DNA Preparation.

2 ml anaerobic fully grown bacterial culture was prepared as described in (BG10 patent) and extractions were carried out using Thermo Scientific Gene Jet DNA Purification kit, as described by the manufacturer. Eluted, extracted DNA had a concentration of 20 ng/µL in a final volume of 100 µL.

MDA Droplet Generation and Droplet Amplification.

The sample DNA is diluted to $5 \times 10^{-4}$ and 1 µL is mixed with random Exo-resistant heptamer and Exo-resistant hexamer primers in annealing buffer (SampliPhi), and primers are annealed to the template by raising the temperature to 94° C. for 3 minutes and then gradually decreasing the temperature to 20° C. by using a BioRad MyCycler PCR machine at a ramp rate of 5° C./min. Having reached a temperature of 20° C. the mixture was transferred to ice. Phi29 reaction buffer, dNTP, Water, and Phi29 polymerase was added to the mixture as described in Example 1 (701).

Droplet generation oil was added to the reaction tube, and droplets were generated by vortex treatment for 2 minutes, at 3000 RPM (yelp Scientifica) (702). Huge droplets were size excluded, by pumping the entire volume through a funnel in a micro reaction chamber, and only droplets smaller than 5 nL were allowed to continue to the amplification step. Size excluded droplets were discarded (704).

The droplets having successfully passed size exclusion were incubated at 30° C. for 2 hours, and the amplification process was thereafter terminated by raising the temperature to 65° C. for 5 minutes.

Primer Design.

Primers are designed manually to target locations approximately 100 bp either in the 5' or the 3' direction of the gap. For gaps larger than 5000 bp two sets of primers were applied with one set of primers on each side of the gap as illustrated in FIG. 6.

```
Primer1-GAP-Fw:
                                          [SEQ ID No. 5]
5'-GAAGGGTGACAGGATTGATAC Primer1-GAP-Re:
                                          [SEQ ID No. 6]
5'-CGGATTTCCTCCTTTCTATTCC Primer2-GAP-Fw:
                                          [SEQ ID No. 7]
5'-GCCTTGCAAATTCTACATTGACAG Primer2-GAP-Re:
                                          [SEQ ID No. 8]
5'-CCAAGAAAATCATGGGAGATAGTTC
```

Droplet Fusion

Ten combinations of dUTP reaction mixtures (#1-#10) each containing 5-6 pairs of designed primers (10 pmol/µL each) were developed in silico from the GAP-filled paired-end genomic sequence and each combination contained 10-12 primers. The primer combinations were kept in separate liquid solutions and aligned sequentially and thereafter combined with each of the MDA droplets, by merging droplets and PCR-liquids sizes as described in [15] (705). The resulting final droplet sizes ranged between 10-20 nL. All merged droplets were then collected in one reaction tube, and the dUTP-PCR reaction was initiated, as described below.

dUTP-PCR

PCR amplification was performed on all merged droplets in one single tube, carried out as a two stage PCR in a MyCycler PCR machine (BioRad) with the following cycling parameters: 94° C. (15 sec), 25 cycles consisting of a 15 second denaturation at 94° C. and a 15 second extension at 72° C. (706). Following PCR amplification 50,087 droplets were analysed and 1,807 were selectively sorted using micro fluidics device for measurements and isolation as described in [15] (707).

UDG-Treatment

Droplet oil was removed by adding SDS to a final concentration of 10% (w/w) to the reaction and thereafter adding Ammonium Acetate to a final concentration of 2M. The solution was placed on ice for 5 minutes, and was then precipitated by centrifugation at 16.000 G for 10 minutes at 4° C. The double volume of 7M Guanidine-HCl was added, and the mixture was cleaned up using a clean-up spin column (GeneJet DNA extraction, Thermo Scientific). One wash procedure was applied using the wash buffer included in the DNA extraction kit. 20 µL eluted DNA was subsequently treated with UDG (Thermo Scientific) as described by the manufacturer and the reaction was terminated by heat inactivation at 95° C. for ten minutes. The resulting product was ethanol precipitated by centrifugation, and the DNA pellet was thereafter re-suspended in 5 µL (5 mM) Tris buffer.

Pre-Sequencing Amplification and Genome Assembly

The total volume of 5 µL (UDG treated and precipitated) DNA template was used as template in a SampliPhi re-amplification in a total volume of 50 µL to create a total of 1 µg amplified DNA (708). The total volume was nucleotide sequenced by Eurofins Genomic (Ebersberg, Germany) (710), and the assembly of the initial gap-filled genomes and the obtained GAP genome data were carried out using CLC Genomics Workbench version 6.0.4 for genome assembly at default parameters. The final result showed a complete assembly of the genome and the final circular genome sequence was found to have a total of 2,451,061 nucleotides. The closed GAP sequence is given as GAP in [SEQ IN No: 9].

Example 3—Amplifying a Specific Sub Population in a Mixture (*Staphylococcus*)

The current example illustrates how droplet based SampliPhi can be used to isolate DNA from a specifically targeted sub-group of a mixed sample, while still maintaining the original variation in the sample. In this example Staphylococci are targeted by specific primers. Droplets selectively amplified with these primers are isolated and finally PCR spanning the complete 16S rRNA conserved sequence, the intergenic transcribed spacers (ITS) between the 16S and 23S rRNA and the conserved 23S rRNA gene region is used for classification to create a high resolution phylogenetic analysis.

Specific Primer Design

Primers targeting 16S ribosomal DNA of Staphylococci were designed using Primrose primer design software [16]. The conserved regions of the 16S genes were targeted by specific primers Staph-Fw: 5'-AGA CTG GGA TAA CTT CGG GA-3' [SEQ ID NO: 3], and Staph-Re: 5'-CGT CTT TCA CTT TTG AAC CAT GC-3' [SEQ ID NO: 4] generating a PCR product of 76 bp.

Sample Preparation.

A swab sample from a supposed infected tissue from a volunteer was used as template, and DNA was extracted using GeneJet Genomic DNA purification (Thermo Scientific). A preliminary PCR was used to verify the presence of the targeted DNA sequence (*Staphylococcus aureus*). A 10-fold dilution series was used for verification of quantity, based on Cq-values from RT-PCR analysis together with melt curve characteristics. MPN, as described by Garcia-Armisen et al. [17] was used to convert the obtained PCR results to an estimated target quantity. A total quantity of approx. 8,300 16S rRNA gene copies were re-calculated to 1,709 targeted Staphylococci per µL, as each bacterial target is estimated to have an average of 5.5 copies of 16S rRNA genes (701).

Droplet Formation

A 20 µL SampliPhi mixture containing 1 µL DNA template was prepared and added to a droplet generator as described in Example 1, generating approximately 20,000 droplets, each with 1 nL of SampliPhi Phi29 reaction mixture (502). The reaction was incubated for 2 hours, at 30° C. (504) and the temperature was subsequently lowered to +4° C. to halt the reaction.

Droplet Fusion.

Immediately following finalized amplification, each droplet was merged with 9 nL RT-PCR mixture to establish a reaction volume of 10 nL, with RT-mixture (SSO Advance Supermix, BioRad) providing all required PCR reaction components. The SSO Advance supermix was prepared as described by the manufacturer supplemented with specific primers (Staph-F [SEQ ID NO: 3]+Staph-R [SEQ ID NO: 4]) (505).

The total collection of merged droplets (approx. 10 nl/droplet) were separated into 5 PCR tubes, each with 40 µL reaction volume corresponding to approx. 5,000 droplets in each tube. Specific amplification with *Staphylococcus aureus* specific primers was then carried out in each of the five PCR tubes in a PCR machine (BioRad Connect) where cycle conditions were: 30 cycles of (94° C., 60° C., 72° C.) with each temperature interval maintained for 15 seconds (506). After amplification, droplets were screened for successful reaction using fluorescence activated droplet sorting (FADS) as described by [18] (507). The number of positive reactions was 1,562 in a total of 20,238 droplets analyzed, and all droplets with a monitored positive reaction (Sybr-Green fluorescence) were collected in a separate reaction tube.

Cleanup & Re-Amplification.

Sorted SampliPhi amplified droplets were extracted using a spin column DNA extraction procedure described by Yu et al. [19]. The procedure results primarily in purification of products larger than 100 bp as a result of size-dependent binding efficiency of the silica membrane applied during cleanup. Consequently, mainly DNA products of sizes >100 bp are purified during cleanup. Thus, close to all PCR products were removed from amplification, whereas Phi29 amplified DNA was easily recovered. 10 µL eluted DNA (depleted of PCR-products due to PCR product size) were re-amplified by adding the entire volume to a SampliPhi reaction of 50 µL (508). The final product was measured to have a concentration of 220 ng/µL corresponding to a total amount of 11 µg DNA. The nucleotide sequence of the final product was determined.

Results—Example 3

A 16S rRNA clone library study of the sequence of the obtained DNA revealed that all 16S rRNA genes were identical and that they could be assigned to the *Staphylococcus* genus and, thus, it was concluded that the studied infection originated from one single strain of *staphylococcus* (FIG. 8) [SEQ ID: 10]. Moreover, the resolution of the sequence data obtained during this study strengthens the degree of phylogenetic similarity of the obtained sequences illustrating a clonal distribution rather than a multiplex infectious culture, as all obtained sequences were 100% identical. The combined analysis results, where both 16S rRNA and 23S rRNA genes were present, provide a high accuracy of phylogenetic grouping even if distantly related bacteria were present in the analyzed sample. In addition, as the highly variable ITS region between the 16S rRNA and 23S rRNA genes was also included in the analysis, the illustrated example also provides information to distinguish even extremely closely related strains. We have used that information to distinguish between an outbreak of an infectious disease of clonal origin, and an infection initiated from multiple strains.

Assembly of the sequences demonstrated a close to complete elimination of the generated PCR products from the droplet screening procedure. Although the small sizes of PCR products present an effect on silica based purification, it is surprising that also the Phi29 reaction seemingly does not initiate displacement amplification, probably due to the lack of sufficiently large sized template. Phi29 amplification is known to be efficient when amplifying large pieces of DNA while amplification of DNA molecules of 76 bp is practically impossible.

Example 4—Amplifying a Specific *E. coli* Gene from a Mixture of *E. coli* and HeLa DNA The current example illustrates how droplet based SampliPhi was used to isolate DNA from a specifically targeted DNA sequence (ThrA gene from *E. coli*) in a sample where non-target background (HeLa) DNA initially is abundant. Droplets with Phi29 (Enzymatics) reaction components were generated using a droplet generation chip creating mono disperse droplets of approximately 800-900 pl in a fluorocarbon carrier oil. PCR ingredients were added to each droplet and those droplets where the target sequence was present were amplified by PCR and thereafter detected as fluorescent droplets and collected using a microfluidic device for sorting.

Phi reaction was set up by adding 1 µL DNA template to a total volume of 20 µl (×1 Phi29 reaction buffer, 0.05 mM dNTP, 1 µl (ready to use)×1 Random Hexamer primers (Thermo Scientific), 0.25 µl Phi29 polymerase (Enzymatics). The mixture was then distributed into aqueous droplet aliquots of approximately 700-800 pl each by separating the Phi reaction by fluorocarbon oil using a microfluidics droplet device. The droplets were thereafter incubated at 30° C. for 4 hours.

After droplet formation and subsequent incubation, a mixture of PCR ingredients was merged into each of the droplets and a specific detection was carried out using an optimized PCR system with a molecular beacon used as reporter molecule. In this example E. coli aspartokinase (ThrA) was targeted by specific primers (MB8 fw1 & MB8 Re1) and a specific molecular beacon (MB8.9) designed to anneal to the DNA sequence between the two specific primers. Those droplets, where a specific amplification was not observed are then selectively removed using a micro fluidic device, and the content of the collected droplets were re-amplified to reach sufficient amount of DNA to enable sequencing.

Specific Primer Design

Primers and beacon targeting the thrA region of E. coli were designed manually. Beacon folding structure was verified using mFold software [20].

```
MB8 fw1:
                                            [SEQ ID: 11]
5'-GACGGTAGATTCGAGGTAATGC-3'

MB8 Re1:
                                            [SEQ ID: 12]
5'-TATGGCCGGCGTATTAGAAG-3'.

MB8.9:
                                            [SEQ ID: 13]
5'(HEX)-CGTTTGTGTTTTCGACCGGATCGATAACAGTAA
CG-3'(BHQ).
```

Sample Preparation.

DNA from E. coli (Life Technologies) and HeLa (Promega) were mixed in final concentrations of 1 µg/µl E. coli and 4 µg/µl Hela. From calculations based on genome size this mixture contains approximately 200 copies of the targeted gene (ThrA) pr. µl and Real Time PCR measurements confirmed the initial amount of target to be 200 target copies/pg.

Droplet Formation

A 15 µL Phi29 mixture containing 1 µL DNA sample was prepared and added to a droplet generator as described in Example 1. The procedure generated approximately 16.500 droplets, each with 800-900 pL of Phi29 reaction mixture. Droplet generation was carried out at 4° C. to ensure that amplification would not occur in the system prior to droplet generation. The reaction was then incubated for 4 hours, at 30° C.

Droplet Fusion.

Immediately after finalized amplification, each Phi29 droplet was merged with 4 nL PCR mixture containing (×1 PCR buffer, 0.1 mM dNTP, 0.2 mM Mg+, 0.05 U GoTaq2, 0.025 pmol/µl MB8-Fw1, 0.025 pmol/µl MB8-Re1, 0.018 pmol/µl MB8.9-BHQ-HEX) using a x-junction chip for merging. The total collection of merged droplets (approx. 5 nl/droplet) was pumped into a 2 reagent droplet chip (gate size: 50 µm) used to create a total of 210.000 droplets with an average size of 80 pl. PCR amplifications in each merged and re-droplet formed droplets were carried out in a standard PCR machine (MyCycler, BioRad) using a two-step amplification protocol: 95° C. (2 min)+35 cycles of 94° C. (3 sec)+56° C. (15 sec). Those droplets where a target template had initially been amplified generated a strong fluorescent signal easily distinguishable from those droplets where no specific target was present. Discrimination between positive and negative droplets was done using a standard fluorescence microscope (Nikon) with a HEX-fluorescence emission source and detection filter.

The amplified droplets were pumped through the detection/collection section of a droplet generation chip (100 µm X-gate, 2-reagent droplet chip) used for sorting and a total of 50 droplets were collected by applying sufficient suction to an empty channel to ensure isolation of the positive droplets while discarding negative droplets.

Cleanup & Reamplification

The collected droplets were retrieved from the microfluidics device by gravity flow and were collected into a 200 µl PCR tube into 50 µl fluorocarbon oil. 10 µl water was added to the tube used for isolation of the aqueous phase of the mixture. Then, 10 µl sample was collected and the entire volume of 10 µl was used as template in a subsequent re-amplification, using identical conditions as mentioned in the initial Phi amplification (Enzymatics).

The final product was measured to a concentration of 330 ng/µL in a total reaction volume of 20 µl. RT-PCR (SSO Advance, BioRad) and total DNA quantification (Promega, BioFluorometer) was used to determine the enrichment, and the final quantity was 3160 target copies/pg corresponding to a target increase of ×79.

Amplified and targeted nucleotide sequence (97 bp):

```
                                            [SEQ ID No: 14]
GACGGTAGATTCGAGGTAATGCCCCACTGCCAGCAGTTTTTCGACCGGA
TCGATAACAGTAACGTTGTGACCGCGCGCTTCTAATACGCCGGCCATA
```

Next generation sequencing (Illumina, 150 bp—paired end Library) was produced from the enriched product and results showed 12.258 bp with coverages ranging from ×4 to ×63. The highest coverage was located at the targeted sequence (Amplified and targeted nucleotide sequence, see above) and the lowest coverage at the furthest 5' end of the assembly. The obtained sequence aligned 100% to the reference genome (Accession no. CP011324) over the full range of the assembly.

REFERENCES

1. Sharma, S., et al., *Droplet-based microfluidics*. Methods in Molecular Biology, 2013. 949: p. 207-30.
2. Hindson, B. J., et al., *High-throughput droplet digital PCR system for absolute quantitation of DNA copy number*. Anal Chem, 2011. 83(22): p. 8604-10.
3. Sambrook, J. and D. W. Russell, *Molecular Cloning a laboratory manual* 2001: Cold Spring Harbor Laboratory Press.
4. Walter, N. G., *Single molecule tools: fluorescence based approaches, part A. Preface*. Methods in Enzymology, 2010. 472: p. xxi-xxii.
5. Kintses, B., et al., *Microfluidic droplets: new integrated workflows for biological experiments*. Current Opinion in Chemical Biology, 2010. 14(5): p. 548-55.
6. Rinke, C., et al., *Obtaining genomes from uncultivated environmental microorganisms using FACS-based single-cell genomics*. Nat. Protocols, 2014.9(5): p. 1038-1048.
7. Raghunathan, A., et al., *Genomic DNA amplification from a single bacterium*. Applied and Environmental Microbiology, 2005. 71(6): p. 3342-3347.
8. Day, P., Manz, A., Zhang, Y., *Microdroplet Technology: Principles and Emerging Applications in Biology and Chemistry*. Integrated analytical systems, ed. R. A. Potyrailo 2012.

9. Longo, M. C., M. S. Berninger, and J. L. Hartley, *Use of uracil DNA glycosylase to control carry-over contamination in polymerase chain reactions*. Gene, 1990. 93(1): p. 125-8.
10. Prodělalová, J., et al., *Isolation of genomic DNA using magnetic cobalt ferrite and silica particles*. Journal of Chromatography A, 2004. 1056(1-2): p. 43-48.
11. Kilstrup, M. and K. N. Kristiansen, *Rapid genome walking: a simplified oligo-cassette mediated polymerase chain reaction using a single genome-specific primer*. Nucleic Acids Res, 2000. 28(11): p. e55.
12. Liu, L., et al., *Comparison of next-generation sequencing systems*. J Biomed Biotechnol, 2012. 2012: p. 251364.
13. Kvist, T., et al., *Diversity of thermophilic and non-thermophilic crenarchaeota at 80 degrees C*. FEMS Microbiol. Lett., 2005. 244(1): p. 61-68.
14. Pan, X., et al., *A procedure for highly specific, sensitive, and unbiased whole-genome amplification*. Proceedings of the National Academy of Sciences, 2008. 105(40): p. 15499-15504.
15. Brouzes, E., et al., *Droplet microfluidic technology for single-cell high-throughput screening*. Proceedings of the National Academy of Sciences, 2009. 106(34): p. 14195-14200.
16. Ashelford, K. E., A. J. Weightman, and J. C. Fry, *PRIMROSE: a computer program for generating and estimating the phylogenetic range of 16S rRNA oligonucleotide probes and primers in conjunction with the RDP-II database*. Nucleic Acids Res., 2002. 30(15): p. 3481-3489.
17. Garcia-Armisen, T. and P. Servais, *Enumeration of viable E. coli in rivers and wastewaters by fluorescent in situ hybridization*. J Microbiol. Methods, 2004. 58(2): p. 269-279.
18. Baret, J. C., et al., *Fluorescence-activated droplet sorting (FADS): efficient microfluidic cell sorting based on enzymatic activity*. Lab Chip, 2009. 9(13): p. 1850-8.
19. Yu, Z. and W. Mohn, *Killing two birds with one stone: simultaneous extraction of DNA and RNA from activated sludge biomass* Canadian Journal of Microbiology, 1999. 45(3): p. 269-272.
20. Zuker, M., *Mfold web server for nucleic acid folding and hybridization prediction*. Nucleic Acids Res, 2003. 31(13): p. 3406-15.

The invention claimed is:

1. An in vitro method for enriching for one or more target DNA molecules from a sample of mixed DNA molecules comprising the steps of:
   a) providing a liquid sample of mixed DNA molecules comprising non-target DNA molecules and one or more specific target DNA molecules and reagents for general amplification of DNA (401),
   b) formation of a multiple of liquid droplets each comprising mixed DNA molecules from said liquid sample (403),
   c) general amplification of said non-target and target DNA molecules in the multiple of droplets, wherein each droplet contains less than 0.5 of said one or more target DNA molecules on average (404),
   d) specific detection of said one or more target DNA molecules in droplets containing at least one of said target DNA molecules (405), and
   e) physically selecting droplets containing at least one of said target DNA molecules (406), wherein the frequency of the target DNA molecule compared to its frequency in the sample of mixed DNA molecules in step (a) is increased between 0.1×(number of droplets without target DNA)×(number of droplets with target DNA)−1 and 10×(number of droplets without target DNA)×(number of droplets with target DNA)−1.

2. The method according to claim 1, wherein the total number of droplets is at least 10,000.

3. The method according to claim 1, wherein reagents for specific detection of said one or more target DNA molecules are added to said multiple of droplets after said general amplification in step c) (505).

4. The method according to claim 1, wherein reagents for specific detection of said one or more target DNA molecules are comprised in said sample (401).

5. The method according to claim 1, wherein said one or more target DNA molecules comprise one or more unique consecutive sequence of at least 10 nucleotides.

6. The method according to claim 1, wherein the general amplification of DNA in step (c) is performed by a technique selected from the following: randomly degenerate primed PCR, linker ligation PCR, Degenerate Oligonucleotide Primed (DOP) PCR and/or Multiple Displacement Amplification.

7. The method according to claim 1, wherein the specific detection is performed using PCR.

8. The method according to claim 3, wherein the reagents for specific detection contain dUTP.

9. The method according to claim 1, further comprising step (f), comprising: inactivating, degrading and/or removing DNA produced for specific detection of said one or more target DNA molecules.

10. The method according to claim 9, wherein the inactivation is performed using uracil-DNA N-glycosylase.

11. The method according to claim 1, further comprising step (g), comprising: repeating steps (a) to (e), wherein the mixed DNA molecules comprising the non-target and target DNA molecules in said liquid sample of repeated step (a) are derived from the droplets containing the at least one of said target DNA molecules selected in step (e).

12. The method according to claim 1, further comprising step (h), comprising: amplification of the at least one of said target DNA molecules comprised in droplets obtained in step (e).

13. The method according to claim 1, wherein said one or more target DNA molecules comprise 1,000 to 100,000 nucleic acid base pairs.

14. The method according to claim 1, wherein the one or more target DNA molecules are derived from the genome of a cell.

15. The method according to claim 1, wherein said droplets formed in step b) contain on average less than 0.5 target DNA molecule per droplet.

* * * * *

UNITED STATES PATENT AND TRADEMARK OFFICE
CERTIFICATE OF CORRECTION

PATENT NO. : 10,704,080 B2  
APPLICATION NO. : 15/317050  
DATED : July 7, 2020  
INVENTOR(S) : Marie Just Mikkelsen and Thomas Kvist Page 1 of 1

It is certified that error appears in the above-identified patent and that said Letters Patent is hereby corrected as shown below:

In the Claims

In Column 39, Claim 1, Lines 39-46, each instance of "-1" should read -- $^{-1}$ --.

Signed and Sealed this  
Twenty-sixth Day of January, 2021

Drew Hirshfeld  
*Performing the Functions and Duties of the*  
*Under Secretary of Commerce for Intellectual Property and*  
*Director of the United States Patent and Trademark Office*